United States Patent
Li et al.

(10) Patent No.: US 10,013,528 B2
(45) Date of Patent: Jul. 3, 2018

(54) MEDICAL IMAGE STORING METHOD, INFORMATION EXCHANGING METHOD, AND APPARATUSES

(71) Applicant: Huawei Technologies Co., Ltd., Shenzhen (CN)

(72) Inventors: Yingtao Li, Shenzhen (CN); Shanfu Li, Shenzhen (CN); Kangmin Huang, Shenzhen (CN)

(73) Assignee: HUAWEI TECHNOLOGIES CO., LTD., Shenzhen (CN)

(*) Notice: Subject to any disclaimer, the term of this patent is extended or adjusted under 35 U.S.C. 154(b) by 37 days.

(21) Appl. No.: 15/245,572

(22) Filed: Aug. 24, 2016

(65) Prior Publication Data
US 2016/0364529 A1 Dec. 15, 2016

Related U.S. Application Data

(63) Continuation of application No. PCT/CN2014/090089, filed on Oct. 31, 2014.

(30) Foreign Application Priority Data

Feb. 25, 2014 (CN) .......................... 2014 1 0065001

(51) Int. Cl.
*G06K 9/00* (2006.01)
*G06F 19/00* (2018.01)
(Continued)

(52) U.S. Cl.
CPC .......... *G06F 19/321* (2013.01); *G06K 9/6215* (2013.01); *G06T 7/0016* (2013.01);
(Continued)

(58) Field of Classification Search
CPC .............. G06K 9/00; G06T 7/00; G06F 19/00
(Continued)

(56) References Cited

U.S. PATENT DOCUMENTS 6,475,146 B1* 11/2002 Frelburger ........... A61B 5/0002
600/437
7,130,460 B2* 10/2006 Nakazawa .............. G06T 5/004
382/128
(Continued)

FOREIGN PATENT DOCUMENTS

CN 101097628 A 1/2008
CN 101238987 A 8/2008
(Continued)

OTHER PUBLICATIONS

Machine Translation and Abstract of Chinese Publication No. CN101238987, Aug. 13, 2008, 8 pages.
(Continued)

*Primary Examiner* — Abolfazl Tabatabai
(74) *Attorney, Agent, or Firm* — Conley Rose, P.C.

(57) ABSTRACT

The present disclosure discloses a medical image storing method, an information exchanging method, and apparatuses. A method includes: acquiring a medical image and a reference image, where the medical image and the reference image are images of a same region of a first object that are photographed at different times; determining an increment of the medical image relative to the reference image; and storing the increment of the medical image relative to the reference image. According to some embodiments of the present disclosure, an increment of a medical image relative to a reference image is determined, and only the reference image and the increment of the medical image relative to the reference image are stored, thereby reducing storage space occupied by a medical image.

13 Claims, 9 Drawing Sheets

(51) Int. Cl.
- *G06K 9/62* (2006.01)
- *G06T 7/00* (2017.01)
- *G06T 7/254* (2017.01)
- *G16H 40/20* (2018.01)
- *G01N 23/04* (2018.01)

(52) U.S. Cl.
CPC .............. *G06T 7/254* (2017.01); *G16H 40/20* (2018.01); *G06T 2207/10056* (2013.01); *G06T 2207/10072* (2013.01); *G06T 2207/10081* (2013.01); *G06T 2207/10088* (2013.01); *G06T 2207/10116* (2013.01); *G06T 2207/30048* (2013.01); *G06T 2207/30096* (2013.01)

(58) Field of Classification Search
USPC ..................................... 382/128–134; 378/62
See application file for complete search history.

(56) References Cited

U.S. PATENT DOCUMENTS

| | | | |
|---|---|---|---|
| 2003/0130870 A1* | 7/2003 | Tsuchimura | G06F 19/327 705/2 |
| 2009/0146950 A1* | 6/2009 | Maringelli | G06F 19/3406 345/158 |
| 2013/0345563 A1 | 12/2013 | Stuebe et al. | |

FOREIGN PATENT DOCUMENTS

| | | |
|---|---|---|
| CN | 101243980 A | 8/2008 |
| CN | 101578630 A | 11/2009 |
| CN | 101968889 A | 2/2011 |
| CN | 102438502 A | 5/2012 |
| CN | 102866872 A | 1/2013 |
| CN | 102920439 A | 2/2013 |
| CN | 103310109 A | 9/2013 |
| CN | 103505244 A | 1/2014 |
| CN | 103514359 A | 1/2014 |
| WO | 2013111033 A2 | 8/2013 |

OTHER PUBLICATIONS

Machine Translation and Abstract of Chinese Publication No. CN102920439, Feb. 13, 2013, 4 pages.
Machine Translation and Abstract of Chinese Publication No. CN103310109, Sep. 18, 2013, 8 pages.
Machine Translation and Abstract of Chinese Publication No. CN103514359, Jan. 15, 2014, 5 pages.
Foreign Communication From a Counterpart Application, PCT Application No. PCT/CN2014/090089, International Search Report dated Feb. 11, 2015, 3 pages.
Foreign Communication From a Counterpart Application, PCT Application No. PCT/CN2014/090089, Written Opinion dated Feb. 11, 2015, 11 pages.
Machine Translation and Abstract of Chinese Publication No. CN101968889, Feb. 9, 2011, 25 pages.
Machine Translation and Abstract of Chinese Publication No. CN102866872, Jan. 9, 2013, 19 pages.
Foreign Communication From a Counterpart Application, Chinese Application No. 2014100650014, Chinese Search Report dated Nov. 6, 2017, 2 pages.
Foreign Communication From a Counterpart Application, Chinese Application No. 2014100650014, Chinese Office Action dated Nov. 14, 2017, 6 pages.

* cited by examiner

MEDICAL IMAGE STORING METHOD, INFORMATION EXCHANGING METHOD, AND APPARATUSES

CROSS-REFERENCE TO RELATED APPLICATIONS

This application is a continuation application of international application number PCT/CN2014/090089 filed on Oct. 31, 2014, which claims priority to Chinese patent application number 201410065001.4 filed on Feb. 25, 2014, both of which are incorporated by reference.

TECHNICAL FIELD

The present disclosure relates to the field of image processing technologies, and in particular, to a medical image storing method, an information exchanging method, and apparatuses.

BACKGROUND

At present, a quantity of examination images of patients stored by an existing medical device is relatively limited, and retention time is relatively short. A main reason is that a medical device needs to store a large quantity of medical images and requires large storage space. Besides, because storage of a medical image mainly focuses on compression of a single image, and a compression ratio is limited, data of a medical image is excessively large, which also requires larger storage space.

SUMMARY

Embodiments of the present disclosure provide a medical image storing method, an information exchanging method, and apparatuses, which can reduce storage space occupied by a medical image.

According to a first aspect, a medical image storing method is provided, where the method includes: acquiring a medical image and a reference image, where the medical image and the reference image are images of a same region of a first object that are photographed at different times; determining an increment of the medical image relative to the reference image; and storing the increment of the medical image relative to the reference image. With reference to the first aspect, in a first possible implementation manner of the first aspect, the method further includes: determining, according to a photographing time or photographing frequency, to use a medical image of the same region of the first object as the reference image.

With reference to the first aspect, in a first possible implementation manner, the determining an increment of the medical image relative to the reference image includes: performing residual processing or variance processing on the medical image and the reference image, to obtain the increment of the medical image relative to the reference image.

With reference to the first aspect or the first possible implementation manner, in a second possible implementation manner, before the determining an increment of the medical image relative to the reference image, the method further includes: adjusting the medical image according to the reference image, where the determining an increment of the medical image relative to the reference image includes: determining an increment of the adjusted medical image relative to the reference image.

With reference to the first aspect or the first or second possible implementation manner, in a third possible implementation manner, the method further includes: determining, according to a photographing time or photographing frequency, to use a medical image of the same region of the first object as the reference image.

With reference to the first aspect or any possible implementation manner of the first to third possible implementation manners, in a fourth possible implementation manner, before the acquiring a medical image and a reference image, the method further includes: acquiring the first photographed medical image of the same region of the first object; and using the first photographed medical image of the same region of the first object as the reference image of a subsequently photographed medical image.

With reference to the first aspect or any possible implementation manner of the first to fourth possible implementation manners, in a fifth possible implementation manner, the method is executed by a server, and the acquiring a medical image and a reference image, includes: receiving, by the server, the medical image by using a network; and acquiring, by the server, the reference image from a database.

With reference to the fifth possible implementation manner, in a sixth possible implementation manner, the receiving, by the server, the medical image by using a network includes: receiving, by the server, a data packet of the medical image by using the network, where the data packet includes the medical image, an identity (ID) of the first object, and information indicating the same region.

With reference to the first aspect or any possible implementation manner of the first to fourth possible implementation manners, in a seventh possible implementation manner, the method is executed by an image collection device, and the acquiring a medical image and a reference image includes: photographing, by the image collection device, the medical image and the reference image.

With reference to the seventh possible implementation manner, in an eighth possible implementation manner, the photographing, by the image collection device, the medical image and the reference image includes: successively photographing, by the image collection device, multiple medical images, where the multiple medical images include the medical image or the reference image.

With reference to the seventh or eighth possible implementation manner, in a ninth possible implementation manner, the image collection device photographs the medical image or the reference image by means of microscope-level micro-photographing or at millisecond-level frequency.

With reference to the seventh or eighth or ninth possible implementation manner, in a tenth possible implementation manner, the method further includes: sending, by the image collection device, the reference image and increments of the multiple medical images relative to the reference image to a server, so that the server provides health advice information for the first object according to the reference image and the increments of the multiple medical images relative to the reference image.

With reference to the eighth or ninth possible implementation manner, in an eleventh possible implementation manner, the method further includes: determining, by the image collection device, a change trend of the multiple medical images according to increments of the multiple medical images relative to the reference image; and sending, by the image collection device, the change trend of the multiple medical images to a server, so that the server provides health advice information for the first object according to the change trend of the multiple medical images.

With reference to the tenth or eleventh possible implementation manner, in a twelfth possible implementation manner, the method further includes: receiving, by the image collection device, a message sent by the server, where the message is health advice for the first object.

According to a second aspect, an information exchanging method is provided, where the method includes: acquiring increments of multiple medical images of a same region of a first object relative to a reference image, where the multiple medical images are stored according to the method in the first aspect or any possible implementation manner of the first to sixth possible implementation manners; determining a change trend of the multiple medical images according to the increments of the multiple medical images relative to the reference image; when the change trend of the multiple medical images exceeds a preset threshold, sending first information to a terminal of the first object, where the first information is used to indicate the change trend of the multiple medical images; and sending appointment information of a medical institution to the terminal of the first object, where the appointment information is used to indicate an available medical resource of the medical institution.

With reference to the second aspect, in a first possible implementation manner of the second aspect, before the sending appointment information of a medical institution to the terminal of the first object, the method in the second aspect further includes: establishing communication with a server of the medical institution, and acquiring the appointment information of the medical institution, where the appointment information includes the following information: a department, a time, and a doctor.

With reference to the second aspect or the first possible implementation manner of the second aspect, in a second possible implementation manner of the second aspect, the method in the second aspect further includes: comparing the change trend of the multiple medical images of the same region of the first object with a change trend of multiple medical images of a same region of a second object, to obtain a similarity degree between the change trends of the multiple medical images of the same regions of the first object and the second object, where the first information is further used to indicate the similarity degree between the change trends of the multiple medical images of the same regions of the first object and the second object.

With reference to the second aspect or the first or second possible implementation manner of the second aspect, in a third possible implementation manner of the second aspect, the method in the second aspect further includes: receiving appointment confirmation information sent by the terminal of the first object; and sending, according to the appointment confirmation information, the change trend of the multiple medical images and the increments of the multiple medical images relative to the reference image to the server of the medical institution confirmed by the first object.

With reference to the second aspect or the first or second or third possible implementation manner, in a fourth possible implementation manner of the second aspect, the multiple medical images are stored according to the method in the first aspect or any possible implementation manner of the first to sixth possible implementation manners of the first aspect.

According to a third aspect, an information exchanging method is provided, where the method includes: acquiring increments of multiple medical images of a same region of a first object relative to a reference image, where the multiple medical images are stored according to the method in the first aspect or any possible implementation manner of the first to sixth possible implementation manners; determining a change trend of the multiple medical images according to the increments of the multiple medical images relative to the reference image; when the change trend of the multiple medical images exceeds a preset threshold, sending first information to a terminal of the first object, where the first information is used to indicate the change trend of the multiple medical images, so that the first object makes an appointment with a medical institution according to the first information; receiving a request message sent by a server of the medical institution with which the first object makes an appointment, where the request message is used to acquire the change trend of the multiple medical images and the increments of the multiple medical images relative to the reference image; and sending the change trend of the multiple medical images and the increments of the multiple medical images relative to the reference image to the server of the medical institution with which the first object makes an appointment.

With reference to the third aspect, in a first possible implementation manner of the third aspect, the method in the third aspect further includes: comparing the change trend of the multiple medical images of the same region of the first object with a change trend of multiple medical images of a same region of a second object, to obtain a similarity degree between the change trends of the multiple medical images of the same regions of the first object and the second object, where the first information is further used to indicate the similarity degree between the change trends of the multiple medical images of the same regions of the first object and the second object.

With reference to the third aspect or the first possible implementation manner of the third aspect, in a second possible implementation manner of the third aspect, the multiple medical images are stored according to the method in the first aspect or any possible implementation manner of the first to sixth possible implementation manners of the first aspect.

According to a fourth aspect, a medical image processing method is provided, where the method includes: acquiring a medical image of a portion of a same region of a first object; acquiring a reference image of a medical image of the same region of the first object; and replacing a part that is in the reference image and corresponds to the medical image of the portion with the medical image of the portion of the same region of the first object, to obtain a new medical image of the same region of the first object.

With reference to the fourth aspect, in a first possible implementation manner of the fourth aspect, the method in the fourth aspect is executed by an image collection device, and the method in the fourth aspect further includes: receiving a notification message sent by a server, where the notification message is used to instruct the image collection device to photograph a medical image of the portion of the same region of the first object; and sending the new medical image of the same region of the first object to the server, where the acquiring a medical image of a portion of a same region of a first object includes: photographing the medical image of the portion of the same region of the first object.

With reference to the fourth aspect, in a second possible implementation manner of the fourth aspect, the method in the fourth aspect is executed by a server, and the method in the fourth aspect further includes: sending a notification message to an image collection device, where the notification message is used to instruct the image collection device to photograph a medical image of the portion of the same region of the first object, where the acquiring a medical image of a portion of a same region of a first object includes: receiving the medical image, which is sent by the image collection device, of the portion of the same region of the first object.

According to a fifth aspect, a medical image storing apparatus is provided, where the apparatus includes: an acquiring module configured to acquire a medical image and a reference image, where the medical image and the reference image are images of a same region of a first object that are photographed at different times; a determining module configured to determine an increment of the medical image relative to the reference image; and a storage module configured to store the increment of the medical image relative to the reference image.

With reference to the fifth aspect, in a first possible implementation manner of the fifth aspect, the determining module is further configured to determine, according to a photographing time or photographing frequency, to use a medical image of the same region of the first object as the reference image.

With reference to the fifth aspect or the first possible implementation manner of the fifth aspect, in a second possible implementation manner of the fifth aspect, the determining module is specifically configured to perform residual processing or variance processing on the medical image and the reference image, to obtain the increment of the medical image relative to the reference image.

With reference to the fifth aspect or the first or second possible implementation manner of the fifth aspect, in a third possible implementation manner of the fifth aspect, the apparatus further includes: an adjustment module configured to adjust the medical image according to the reference image, where the determining module is specifically configured to determine an increment of the adjusted medical image relative to the reference image.

With reference to the fifth aspect or any possible implementation manner of the first to third possible implementation manners of the fifth aspect, in a fourth possible implementation manner of the fifth aspect, before acquiring the medical image and the reference image, the acquiring module is further configured to acquire a second medical image; and the determining module is further configured to use the second medical image as the reference image when the same region of the first object has no reference image.

With reference to the fifth aspect or any possible implementation manner of the first to fifth possible implementation manners of the fifth aspect, in a fifth possible implementation manner of the fifth aspect, the acquiring module is specifically configured to receive the medical image by using a network, and acquire the reference image from a database.

With reference to the fifth possible implementation manner of the fifth aspect, in a sixth possible implementation manner of the fifth aspect, the receiving the medical image by using a network includes: receiving a data packet of the medical image by using the network, where the data packet includes the medical image, an ID of the first object, and information indicating the same region.

With reference to the fifth aspect or any possible implementation manner of the first to fifth possible implementation manners of the fifth aspect, in a seventh possible implementation manner of the fifth aspect, the apparatus is an image collection device, and the acquiring module is specifically configured to photograph the medical image and the reference image.

With reference to the seventh possible implementation manner of the fifth aspect, in an eighth possible implementation manner of the fifth aspect, the acquiring module is specifically configured to successively photograph multiple medical images, where the multiple medical images include the medical image or the reference image.

With reference to the seventh or eighth possible implementation manner of the fifth aspect, in a ninth possible implementation manner of the fifth aspect, the acquiring module photographs the medical image or the reference image by means of microscope-level micro-photographing or at millisecond-level frequency.

With reference to the seventh or eighth or ninth possible implementation manner of the fifth aspect, in a tenth possible implementation manner of the fifth aspect, the apparatus further includes: a sending module configured to send the reference image and increments of the multiple medical images relative to the reference image to a server, so that the server provides health advice information for the first object according to the reference image and the increments of the multiple medical images relative to the reference image.

With reference to the eighth or ninth possible implementation manner of the fifth aspect, in an eleventh possible implementation manner of the fifth aspect, the determining module is further configured to determine a change trend of the multiple medical images according to increments of the multiple medical images relative to the reference image; and the sending module is further configured to send the change trend of the multiple medical images to a server, so that the server provides health advice information for the first object according to the change trend of the multiple medical images.

With reference to the tenth or eleventh possible implementation manner of the fifth aspect, in a twelfth possible implementation manner of the fifth aspect, the apparatus in the fifth aspect further includes: a receiving module configured to receive a message sent by the server, where the message is health advice for the first object.

According to a sixth aspect, an information exchanging apparatus is provided, where the apparatus includes: an acquiring module configured to acquire increments of multiple medical images of a same region of a first object relative to a reference image; a determining module configured to determine a change trend of the multiple medical images according to the increments of the multiple medical images relative to the reference image; and a sending module configured to: when the change trend of the multiple medical images exceeds a preset threshold, send first information to a terminal of the first object, where the first information is used to indicate the change trend of the multiple medical images, and send appointment information of a medical institution to the terminal of the first object, where the appointment information is used to indicate an available medical resource of the medical institution.

With reference to the sixth aspect, in a first possible implementation manner of the sixth aspect, before sending the appointment information of the medical institution to the terminal of the first object, the apparatus in the sixth aspect is further configured to establish communication with a server of the medical institution, and acquire the appointment information of the medical institution, where the appointment information includes the following information: a department, a time, and a doctor.

With reference to the sixth aspect or the first possible implementation manner of the sixth aspect, in a second possible implementation manner of the sixth aspect, the apparatus in the sixth aspect further includes: a comparison module configured to compare the change trend of the multiple medical images of the same region of the first object with a change trend of multiple medical images of a same region of a second object, to obtain a similarity degree between the change trends of the multiple medical images of the same regions of the first object and the second object, where the first information is further used to indicate the similarity degree between the change trends of the multiple medical images of the same regions of the first object and the second object.

With reference to the sixth aspect or the first or second possible implementation manner of the sixth aspect, in a third possible implementation manner of the sixth aspect, the apparatus in the sixth aspect further includes: a receiving module configured to receive appointment confirmation information sent by the terminal of the first object, where the sending module is further configured to send, according to the appointment confirmation information, the change trend of the multiple medical images and the increments of the multiple medical images relative to the reference image to the server of the medical institution confirmed by the first object.

With reference to the sixth aspect or the first or second or third possible implementation manner of the sixth aspect, in a fourth possible implementation manner of the sixth aspect, the multiple medical images are stored by the apparatus according to the fifth aspect or any possible implementation manner of the first to sixth possible implementation manners of the fifth aspect.

According to a seventh aspect, an information exchanging apparatus is provided, where the apparatus includes: an acquiring module configured to acquire increments of multiple medical images of a same region of a first object relative to a reference image; a determining module configured to determine a change trend of the multiple medical images according to the increments of the multiple medical images relative to the reference image; a sending module configured to: when the change trend of the multiple medical images exceeds a preset threshold, send first information to a terminal of the first object, where the first information is used to indicate the change trend of the multiple medical images, so that the first object makes an appointment with a medical institution according to the first information; and a receiving module configured to receive a request message sent by a server of the medical institution with which the first object makes an appointment, where the request message is used to acquire the change trend of the multiple medical images and the increments of the multiple medical images relative to the reference image, where the sending module is configured to send the change trend of the multiple medical images and the increments of the multiple medical images relative to the reference image to the server of the medical institution with which the first object makes an appointment.

With reference to the seventh aspect, in a first possible implementation manner of the seventh aspect, the apparatus in the seventh aspect further includes: a comparison module configured to compare the change trend of the multiple medical images of the same region of the first object with a change trend of multiple medical images of a same region of a second object, to obtain a similarity degree between the change trends of the multiple medical images of the same regions of the first object and the second object, where the first information is further used to indicate the similarity degree between the change trends of the multiple medical images of the same regions of the first object and the second object.

With reference to the seventh aspect or the first possible implementation manner of the seventh aspect, in a second possible implementation manner of the seventh aspect, the multiple medical images are stored by the apparatus in the fifth aspect or any possible implementation manner of the first to sixth possible implementation manners of the fifth aspect.

According to an eighth aspect, a medical image processing apparatus is provided, where the apparatus includes: an acquiring module configured to acquire a medical image of a portion of a same region of a first object, where the acquiring module is further configured to acquire a reference image of a medical image of the same region of the first object; and a replacement module configured to replace a part that is in the reference image and corresponds to the medical image of the portion with the medical image of the portion of the same region of the first object, to obtain a new medical image of the same region of the first object.

With reference to the eighth aspect, in a first possible implementation manner of the eighth aspect, the apparatus in the eighth aspect is an image collection device, and the apparatus in the eighth aspect further includes: a receiving module configured to receive a notification message sent by a server, where the notification message is used to instruct the image collection device to photograph a medical image of the portion of the same region of the first object; and a sending module configured to send the new medical image of the same region of the first object to the server, where the acquiring module includes a photographing unit, further configured to photograph the medical image of the portion of the same region of the first object.

With reference to the eighth aspect, in a second possible implementation manner of the eighth aspect, the apparatus in the eighth aspect is a server, and the apparatus in the eighth aspect further includes: a sending module configured to send a notification message to an image collection device, where the notification message is used to instruct the image collection device to photograph a medical image of the portion of the same region of the first object, where the acquiring module is specifically configured to receive the medical image, which is sent by the image collection device, of the portion of the same region of the first object.

Based on the foregoing technical solutions, an increment of a medical image relative to a reference image is determined, and only the reference image and the increment of the medical image relative to the reference image are stored, thereby reducing storage space occupied by a medical image.

DESCRIPTION OF EMBODIMENTS

In embodiments of the present disclosure, a server is a third-party server that connects a terminal device of a user (for example, a patient) and a medical device of a medical institution. The server may be configured to store a medical image uploaded by a user or a medical institution, and may also store other medical data, including a clinical library, used to store basic information, medical histories, and treatments of patients and examination images stored at different phases according to a medical image storing method in an embodiment of the present disclosure, and a physiological standard library, used to store normal values of physiological parameters of various items such as genders, districts, age groups, and skin colors and normal ranges of incremental change trends of various types of examination images. The server may be a database or an intermediate server (briefly referred to as a Broker). For ease of description, the server is described in the following by using a Broker as an example, but the present disclosure is not limited thereto.

Figure 1:
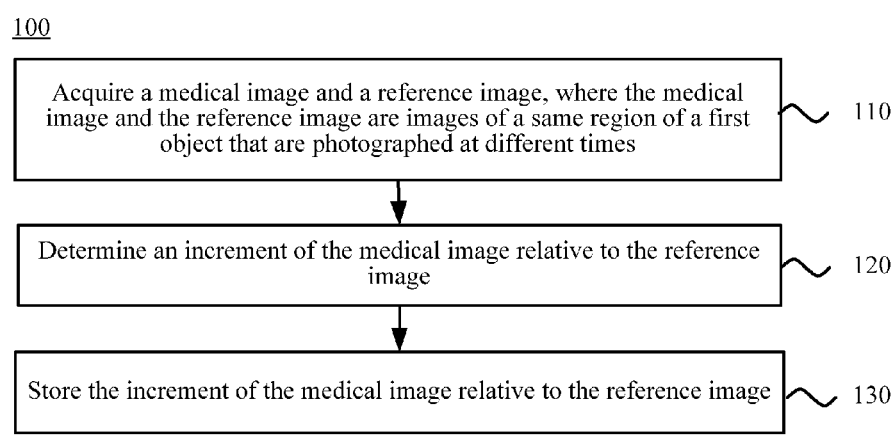
FIG. 1 is a schematic flowchart of a medical image storing method according to an embodiment of the present disclosure.

FIG. 1 is a schematic flowchart of a medical image storing method 100 according to an embodiment of the present disclosure. The method may be executed by a medical device of a medical institution, or may be preferably executed by a server (for example, a Broker), which is not limited in this embodiment of the present disclosure. As shown in FIG. 1, the method 100 includes the following content:

110: Acquire a medical image and a reference image, where the medical image and the reference image are images of a same region of a first object that are photographed at different times.

For example, the first object may be a person (especially a patient) or another organism such as an animal. The medical image may refer to an image of a diseased region, for example, an image of a stomach tumor used to indicate a size of the tumor, but this embodiment of the present disclosure is not limited thereto; for example, the medical image may also be an image of a normal region, for example, an image of a bone used to indicate development of the bone. The images photographed at different times may be images photographed in different years or months or on different days, for example, images of a tumor photographed at intervals of half a year, or may refer to images photographed successively, for example, images of cells in blood photographed at intervals of seconds.

120: Determine an increment of the medical image relative to the reference image.

That is, the reference image is a reference standard when other medical images are stored. For example, the medical image is compared with the reference image, to obtain a difference between the medical image and the reference image or a change in the medical image relative to the reference image.

130: Store the increment of the medical image relative to the reference image.

The reference image and the increment may be stored in a memory of the medical device or the server. Specifically, when the increment of the medical image relative to the reference image is stored, a correspondence between the increment and the reference image is also stored. For example, the correspondence may be stored in a data packet of the increment. When the medical image corresponding to the increment needs to be viewed, the reference image corresponding to the increment is determined according to the correspondence between the increment and the reference image, and after processing is performed on the increment and the reference image, the medical image corresponding to the increment can be restored; or when the increment needs to be analyzed, the increment is directly read from a storage device.

Because the medical image and reference image are photographed for the same region of the first object, the twos images may have a lot of same parts. Therefore, the increment may be very small, which obviously reduces requirements on storage space during storage.

Therefore, according to the medical image storing method in this embodiment of the present disclosure, an increment of a medical image relative to a reference image is determined, and only the reference image and the increment of the medical image relative to the reference image are stored, thereby reducing storage space occupied by a medical image.

Specifically, in this embodiment of the present disclosure, a type of the medical image includes: magnetic resonance imaging (MRI) or computed tomography (CT) or X-ray. This embodiment of the present disclosure is not limited thereto, and the medical image may also be an image obtained by using another imaging device, for example, an image photographed by an ordinary camera or a microscope.

Specifically, in another embodiment of the present disclosure, the method 100 further includes: determining, according to a photographing time or photographing frequency, to use a medical image of the same region of the first object as the reference image.

The reference image may be a fixed image, for example, the first medical image of the same region of the first object, but this embodiment of the present disclosure is not limited thereto; for example, after each preset period, a new medical image is determined to be used as the reference image of a subsequent medical image, or each time after a preset quantity of medical images are photographed, a new medical image is determined to be used as the reference image of a subsequent medical image. For example, determining a reference image according to a photographing time is setting a reference image within a time period. For example, when x-ray images of a leg of a patient are photographed, a same region of the patient needs to be photographed multiple times according to a change in an illness; the medical device or the Broker may be set to set a reference image each half a year, and within the period of half a year, only increments of other images of the same region relative to the reference image are saved. Determining a reference image according to photographing frequency is setting a reference image after a certain quantity of images. For example, the medical device sets a reference image according to photographing frequency, and for a same region, sets a reference image each time after five images are photographed, and stores only increments of the five images relative to the reference image. In a specific embodiment, the same region may also be the entire first object, for example, the entire body of a patient. Therefore, the same region may be understood as a micro region of the first object or the entire first object.

Specifically, in another embodiment of the present disclosure, the determining an increment of the medical image relative to the reference image includes: performing residual processing or variance processing on the medical image and the reference image, to obtain the increment of the medical image relative to the reference image.

For residual processing, for example, a difference, including a luminance value and a chrominance value of a pixel, between each pixel of the reference image and each pixel of the medical image is calculated; for example, a luminance matrix of the reference image is A (a1, a2, a3, ... ), a luminance matrix of each pixel of the medical image is B (b1, b2, b3, ... ), and therefore, an increment $\Delta$ is: $\Delta=A-B$. For variance processing, for example, a luminance matrix of the reference image is A (a1, a2, a3, ... ), a luminance matrix of each pixel of the medical image is B (b1, b2, b3, ... ), and therefore, an increment $\Delta'$ is: $\Delta'=(A-B)^2$.

Further, in this embodiment of the present disclosure, before the determining an increment of the medical image relative to the reference image, the method 100 further includes: adjusting the medical image according to the reference image, where the determining an increment of the medical image relative to the reference image includes: determining an increment of the adjusted medical image relative to the reference image.

In other words, a position and a size of the medical image are adjusted according to the reference image, so that the reference image and the medical image are aligned in a manner that is suitable for comparison. For example, tailoring, rotation, or pixel sampling (upsampling or downsampling) may be performed on the medical image. Besides, an adjustment degree may be selected in a manner of comparing residuals. Tailoring, rotation, and pixel sampling references need to focus on a key part of the medical image, so as to remove some needless parts of the image. The manner of comparing residuals is: comparing residuals, which separately correspond to different sizes of tailoring, different degrees of rotation, and pixel sampling of different filters, between the current medical image and the reference image, and selecting a smallest one: $\Delta=\min\{\Delta \text{rotation}, \Delta \text{tailoring}, \Delta \text{pixel sampling}, ... \}$. In this way, a difference between the adjusted medical image and the reference image is smaller, and therefore, less storage space is occupied.

Besides, in order to accurately determine the increment of the current medical image relative to the reference image, before the image is photographed, it may be required that photographing conditions of the medical image and the reference image are the same. For example, a CT image has coefficients of a window width and a window level, and it may be required that a same window width is used for various examinations of regions, and definitions of window levels of the regions are provided. In this way, when stored according to the method 100, a photographed medical image occupies less storage space, and analysis of a change trend of increments is more accurate.

Optionally, in another embodiment of the present disclosure, before the acquiring a medical image and a reference image, the method 100 further includes: acquiring the first photographed medical image of the same region of the first object; and using the first photographed medical image of the same region of the first object as the reference image of a subsequently photographed medical image.

In other words, when the current medical image has no reference image, the medical image is used as a reference image of a subsequent medical image.

Specifically, in another embodiment of the present disclosure, the method 100 is executed by an image collection device, and the acquiring a medical image and a reference image includes: photographing, by the image collection device, the medical image and the reference image.

The image collection device may be a terminal for home use, or may be a specialized medical photographing device of a medical institution. For example, after photographing a medical image, for medical images of a same region of a same object, the medical photographing device saves only a reference image and an increment of another medical image relative to the reference image, which can reduce storage space of the medical photographing device occupied by a medical image.

More specifically, in another embodiment of the present disclosure, the photographing, by the image collection device, the medical image and the reference image includes: successively photographing, by the image collection device, multiple medical images, where the multiple medical images include the medical image or the reference image.

Specifically, in another embodiment of the present disclosure, the image collection device photographs the medical image or the reference image by means of microscope-level micro-photographing or at millisecond-level frequency.

Specifically, the image collection device may photograph the medical image or the reference image in a manner of microscope-level micro-photographing, or photograph the medical image or the reference image in a manner of millisecond-level frequency photographing. For example, the image collection device may successively photograph the medical image and the reference image at millisecond-level frequency. The reference image is a medical image among multiple medical images successively photographed by the image collection device, for example, the reference image is the first medical image among the multiple medical images that are successively photographed. For a case in which multiple medical images of a same region of a same object need to be successively photographed, the method in this embodiment of the present disclosure can obviously reduce storage space occupied by an image. For example, because a user needs to successively photograph multiple images to observe a change in a sample within a time period, if saving each image causes shortage of storage space, using the medical image storing method in this embodiment of the present disclosure can obviously alleviate the storage problem. For another example, 10 images showing changes in cells in a blood sample are photographed at a high speed, for example, the first photographed image is selected as a reference image, after 9 increments of the remaining 9 images relative to the reference image are determined, only the reference image and the 9 increments need to be saved in a storage unit.

Optionally, in another embodiment of the present disclosure, the image collection device sends the reference image and increments of the multiple medical images relative to the reference image to a server, so that the server provides health advice information for the first object according to the reference image and the increments of the multiple medical images relative to the reference image.

The medical image storing method according to this embodiment of the present disclosure can reduce space occupied by a medical image, but the image collection device has limited storage space and cannot save, in the storage unit of the image collection device, all images that are photographed within a long time period, while the server has large storage space; therefore, the image collection device sends the reference image and the increments to the server, thereby saving the images that are photographed within a long time period. Because only the reference image and the increments of the subsequent medical images relative to the reference image need to be sent to the server, relatively few transmission resources are occupied, and transmission time is shortened.

The image collection device may not store the reference image and the increments of the multiple medical images relative to the reference image, which is not limited in this embodiment of the present disclosure.

Alternatively, in another embodiment of the present disclosure, the method 100 further includes: determining, by the image collection device, a change trend of the multiple medical images according to increments of the multiple medical images relative to the reference image; and sending, by the image collection device, the change trend of the multiple medical images to a server, so that the server provides health advice information for the first object according to the change trend of the multiple medical images.

Optionally, in another embodiment of the present disclosure, the method 100 further includes: receiving a message sent by the server, where the message is health advice for the first object.

For example, after the image collection device sends the reference image and the increments to the Broker or sends the change trend of the medical images to the Broker, the Broker analyzes the reference image and the increments or the change trend of the medical images, and can provide corresponding health advice or doctor-seeing guidance, and send the health advice or the doctor-seeing guidance to the image collection device or a terminal device of a user or a server of a medical institution. The user may go, according to the health advice or the doctor-seeing guidance, to a related medical institution for further health consultation.

Specifically, in another embodiment of the present disclosure, in the method 100, the image collection device may further send the reference image and the increments of the multiple images relative to the reference image to a medical institution selected by a user for an appointment, or send the change trend of the multiple medical images to a medical institution selected by a user for an appointment, so that the medical institution selected by the user for an appointment uses the reference image and the increments or the change trend as a reference for diagnosis.

Specifically, in another embodiment of the present disclosure, the method 100 is executed by a server, and the acquiring a medical image and a reference image includes: receiving, by the server, the medical image by using a network; and acquiring, by the server, the reference image from a database.

For example, the current medical image received by the server by using the network may be uploaded by a user terminal, or may be uploaded by a server of a medical institution. The reference image is previously uploaded by the user terminal or the server of the medical institution.

Specifically, in another embodiment of the present disclosure, the receiving the medical image by using a network includes: receiving a data packet of the medical image by using the network, where the data packet includes the medical image, an ID of the first object, and information indicating the same region.

The data packet may further include information such as a photographing date of the medical image and a type of the medical image, which is not limited in this embodiment of the present disclosure. For example, the foregoing information may be placed in a header of the data packet.

Therefore, according to the medical image storing method in this embodiment of the present disclosure, an increment of a medical image relative to a reference image is determined, and only the reference image and the increment of the medical image relative to the reference image are stored, thereby reducing storage space occupied by a medical image.

Figure 2:
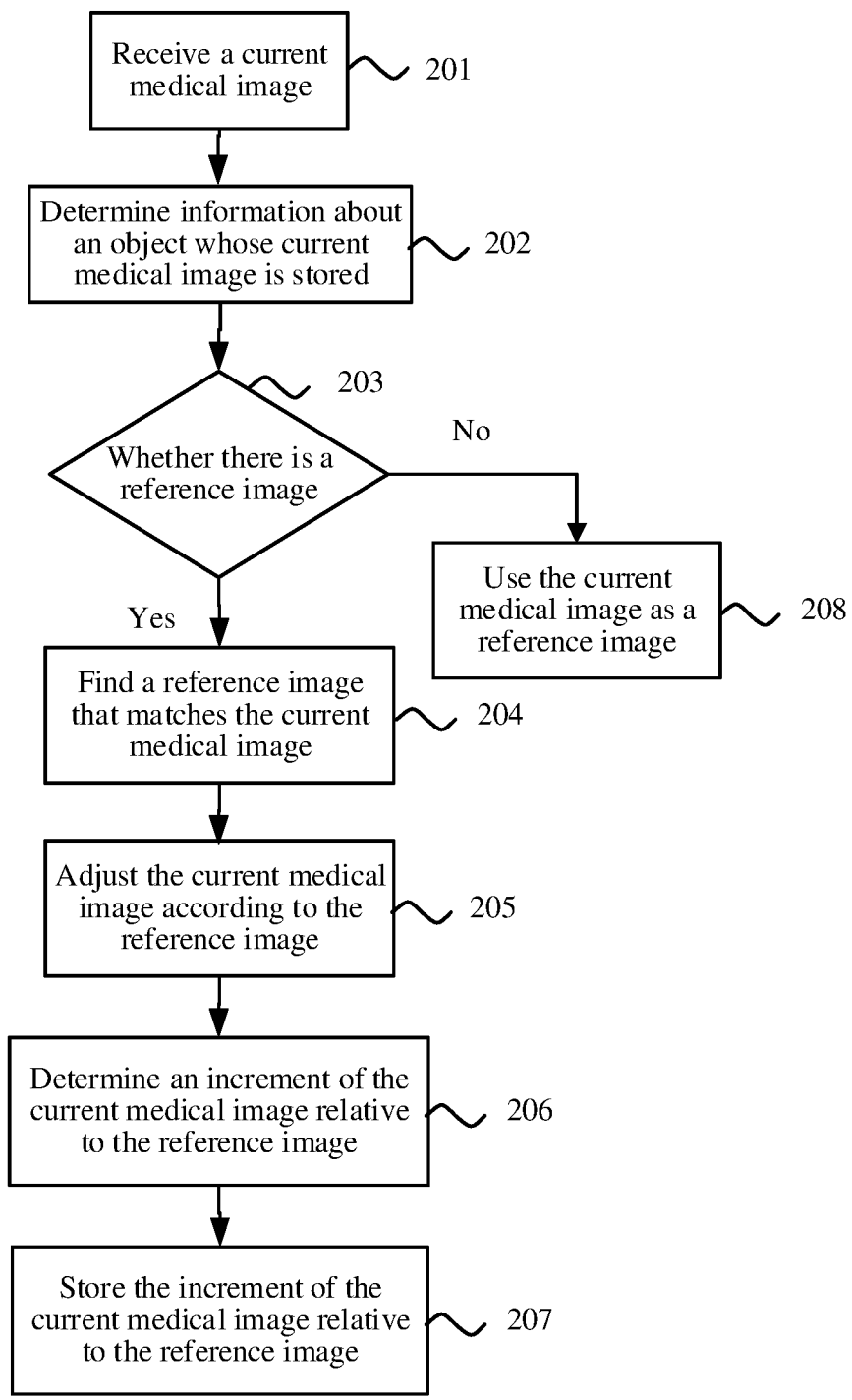
FIG. 2 is a schematic flowchart of a medical image storing method according to another embodiment of the present disclosure.

The following describes the medical image storing method according to this embodiment of the present disclosure in further detail with reference to FIG. 2.

FIG. 2 is a schematic flowchart of a medical image storing method according to another embodiment of the present disclosure. This embodiment is executed by a server, for example, Broker. The method in FIG. 2 is an example of the method in FIG. 1, and detailed descriptions are properly omitted herein. As shown in FIG. 2, the method includes the following content:

201: A server receives a current medical image, which is transmitted by a user or a medical institution by using a network, where a data packet of the transmitted medical image (for example, a header of the data packet) includes information such as an ID indicating a particular patient, an image type (MRI, CT, X-ray, or the like), a diseased region (a body region such as a head or a lung), and a photographing time.

202: The server determines, according to the foregoing information in the header, information about an object whose current medical image is stored.

203: Determine whether the current medical image has a reference image; if the current medical image has a reference image, perform 204; otherwise, perform 208.

For example, if the current medical image is the first medical image of the diseased region, it is determined that the current medical image has no reference image yet.

204: When the server determines that there is a reference image prepared for incremental storing of the current medical image, an image search engine of the server finds, in a storage unit, a reference image that matches the received current medical image.

For example, a suitable reference image may be further searched for and selected according to the ID of the patient, the diseased region, the photographing time, and the image type.

205: Adjust the current medical image according to the reference image.

206: Determine an increment of the current medical image relative to the reference image.

207: Store the increment of the current medical image relative to the reference image, and end the storing process, or continue to perform 201 for receiving a next medical image.

208: Use the current medical image as a reference image, and end the storing process, or continue to perform 201 for receiving a next medical image.

Therefore, according to the medical image storing method in this embodiment of the present disclosure, an increment of a medical image relative to a reference image is determined, and only the reference image and the increment of the medical image relative to the reference image are stored, thereby reducing storage space occupied by a medical image.

Figure 3:
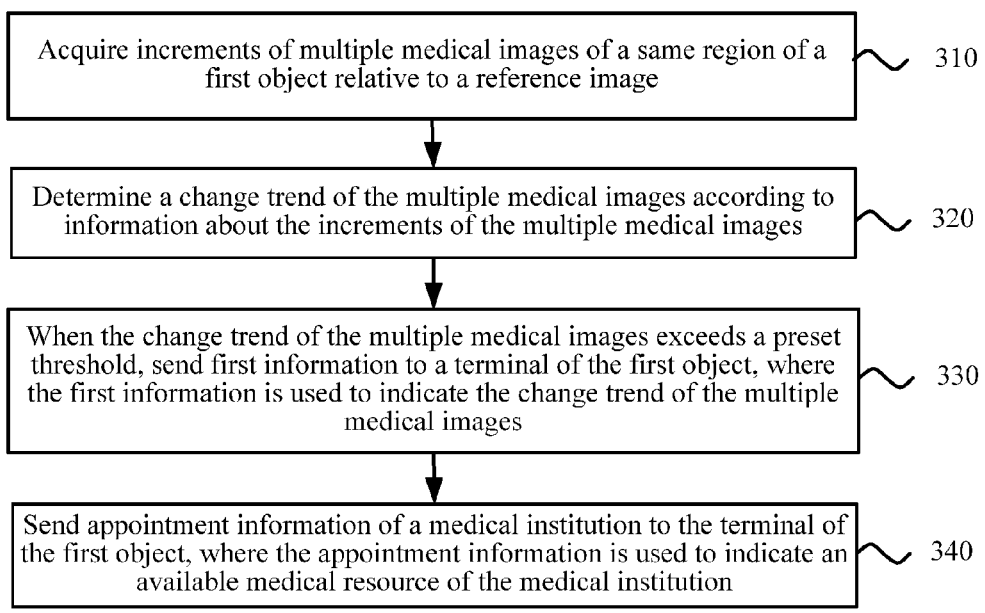
FIG. 3 is a schematic flowchart of an information exchanging method according to an embodiment of the present disclosure.
Figure 4:
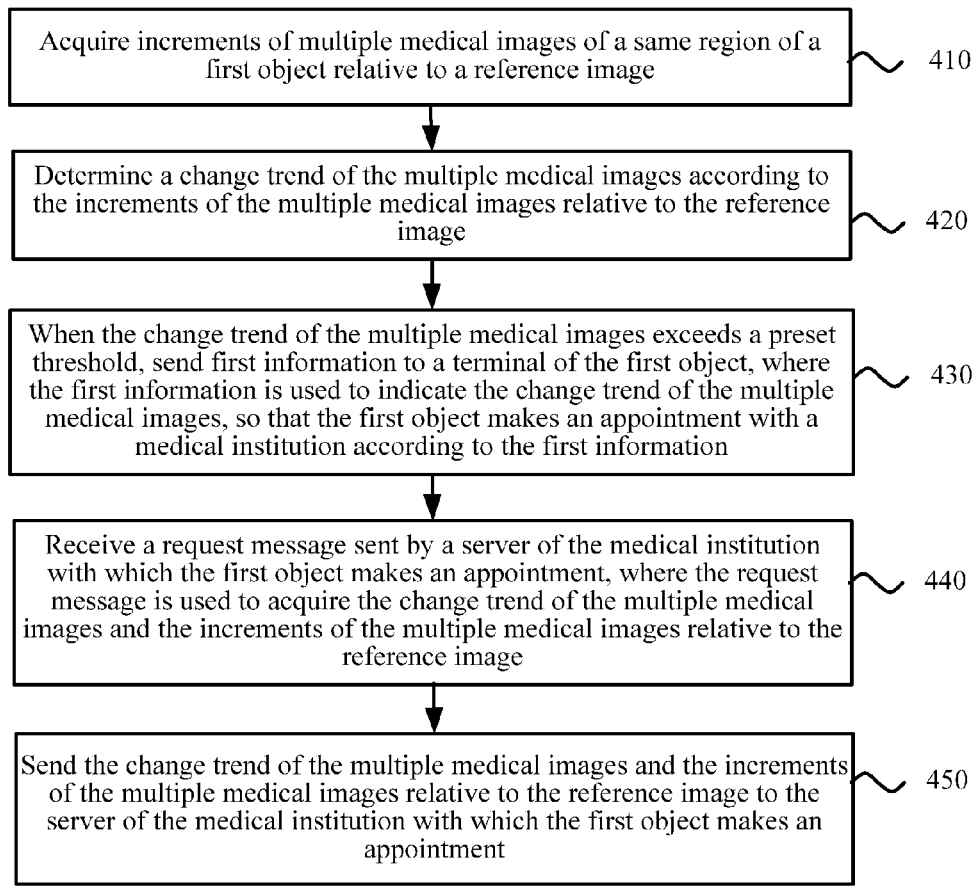
FIG. 4 is a schematic flowchart of an information exchanging method according to another embodiment of the present disclosure.
Figure 5:
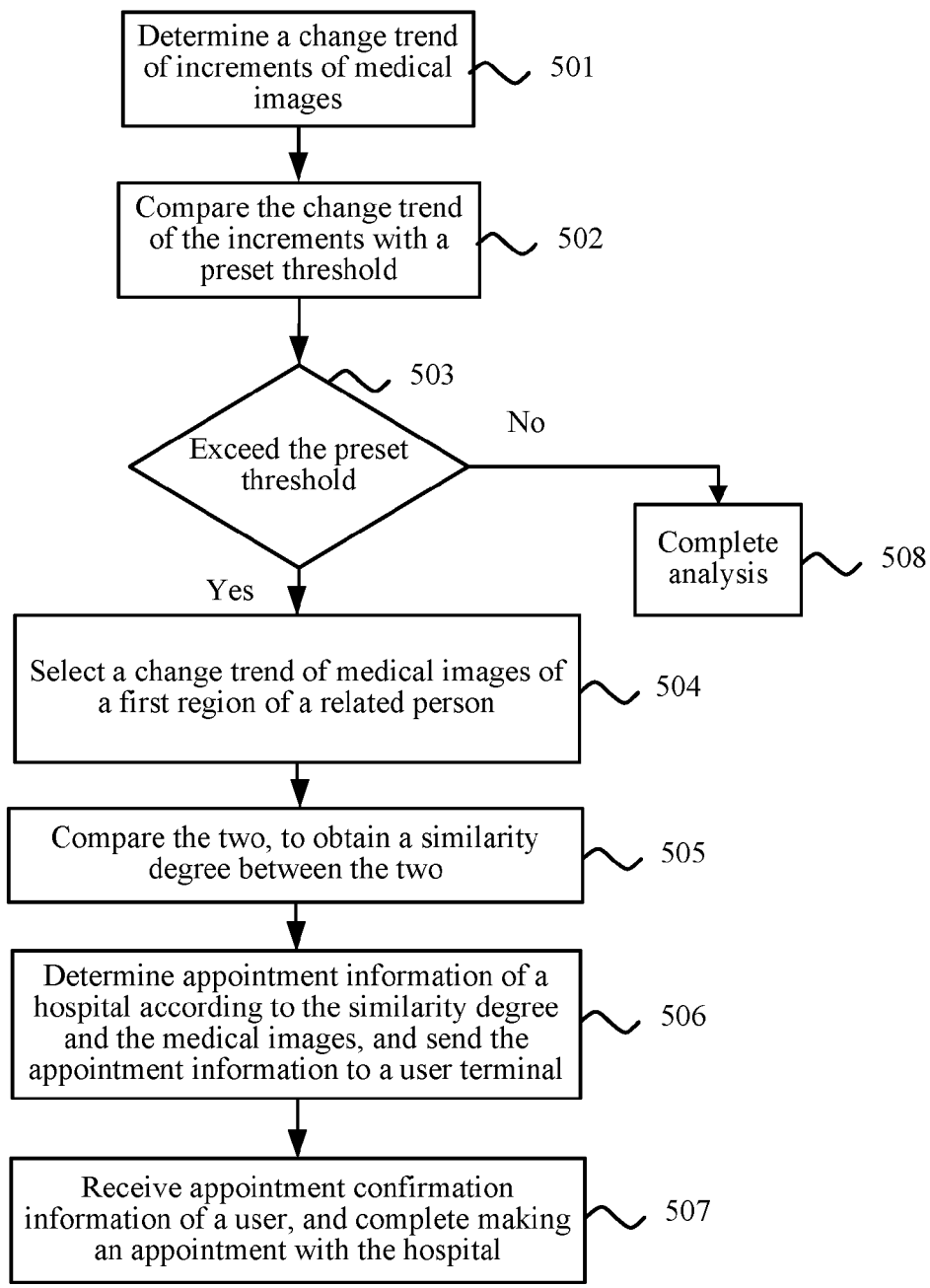
FIG. 5 is a schematic flowchart of an information exchanging method according to another embodiment of the present disclosure.

The foregoing describes the medical image storing methods according to the embodiments of the present disclosure in detail with reference to FIG. 1 and FIG. 2, and the following describes information exchanging methods according to embodiments of the present disclosure in detail with reference to FIG. 3 to FIG. 5.

A Broker may obtain a change trend of medical images of a user through analysis according to stored increments of the medical images, and may further obtain a pathological change in the user through analysis, so as to provide reminding or advice in time for the user or a medical institution uploading the medical images. In this embodiment of the present disclosure, the medical institution may include an institution that can provide disease diagnosis or treatment, such as a hospital, a health institution, or a physical examination center.

FIG. 3 is a schematic flowchart of an information exchanging method 300 according to an embodiment of the present disclosure. The method is executed by a server (for example, a Broker). As shown in FIG. 3, the method 300 includes the following content:

310: Acquire increments of multiple medical images of a same region of a first object relative to a reference image.

320: Determine a change trend of the multiple medical images according to information about the increments of the multiple medical images.

For example, the change trend may be a change in a size of a blood clot in a brain, a change in a tumor size, status of recovery from a fracture, or the like.

330: When the change trend of the multiple medical images exceeds a preset threshold, send first information to a terminal of the first object, where the first information is used to indicate the change trend of the multiple medical images.

The first information may be the change trend of the multiple medical images, or may be information that the change trend of the multiple medical images exceeds the preset threshold. In addition, the first information may be output in a form of an examination report, and the first information may also be displayed on a screen.

340: Send appointment information of a medical institution to the terminal of the first object, where the appointment information is used to indicate an available medical resource of the medical institution.

Specifically, the appointment information of the medical institution may be one piece of appointment information of one doctor of one medical institution, or may be multiple pieces of appointment information of one doctor of one medical institution, or may be multiple pieces of appointment information of multiple doctors of one medical institution, or may be multiple pieces of appointment information of multiple doctors of multiple medical institutions, which is not limited in the present disclosure.

In other words, when the change trend of the multiple medical images of the same region of the first object exceeds the preset threshold, the Broker may actively push the appointment information of the medical institution to the first object.

Therefore, according to the information exchanging method in this embodiment of the present disclosure, increments of multiple medical images of a same region of a first object relative to a reference image are acquired, a change trend of the multiple medical images is determined, first information used to indicate the change trend of the medical images is sent to a terminal of the first object, and appointment information of a medical institution is sent to the terminal of the first object. In this way, the appointment information of the medical institution can be actively pushed to the first object according to the change trend of the medical images of the same region of the first object.

Optionally, in another embodiment of the present disclosure, before the sending appointment information of a medical institution to the terminal of the first object, the method 300 further includes: establishing communication with a server of the medical institution, and acquiring the appointment information of the medical institution, where the appointment information includes the following information: a department, a time, and a doctor.

In other words, after establishing communication with the server of the medical institution, the Broker acquires appointment information, such as a department, a time, and a doctor, corresponding to the same region of the first object from the server of the medical institution. In addition, preferred appointment information may be further acquired according to information about the first object. For example, a medical institution closer to the first object may be further determined according to an address of the first object.

Optionally, in another embodiment of the present disclosure, the method 300 further includes: comparing the change trend of the multiple medical images of the same region of the first object with a change trend of multiple medical images of a same region of a second object, to obtain a similarity degree between the change trends of the multiple medical images of the same regions of the first object and the second object, where the first information is further used to indicate the similarity degree between the change trends of the multiple medical images of the same regions of the first object and the second object.

The second object is an object related to the first object. For example, the second object may be a family member of the first object, or may be an object having a case of illness similar to that of the first object. The change trend of the medical images of the same region of the second object is analyzed, so that the change trend of the same region of the first object can be predicted, to provide corresponding reminding or consultation. For example, the Broker records examination and medical conclusions of a relative related to the first object by blood, and compares examination processes of the first object and the relative related to the first object by blood, to obtain a similarity degree between change trends of medical images of same regions of the two persons through matching, which can help a patient or a doctor to find, as early as possible, a genetic disease that may appear in the first object and provide reminding and health advice.

Optionally, in another embodiment of the present disclosure, the method 300 further includes: receiving appointment confirmation information sent by the terminal of the first object; and sending, according to the appointment confirmation information, the change trend of the multiple medical images and the increments of the multiple medical images relative to the reference image to the server of the medical institution confirmed by the first object.

For example, when the Broker finds that a heart size of a user recently has a continuously increasing trend and the increasing trend exceeds a preset threshold (for example, 1%), the Broker may further obtain through comparison a similarity degree between a change trend of the heart size of the user and a change trend of a heart size of the father, who has a heart disease, of the user, to further determine whether there is a possibility of a genetic disease, or may provide corresponding health consultation for the user according to the similarity degree. At the same time, the Broker determines, according to the change trend of the heart of the user that exceeds the preset threshold, that the user needs to go to a medical institution for a further examination. The Broker selects appointment information of a cardiologist from a medical institution that subscribes to a service of the Broker (a specific manifestation is that the Broker can directly access a resource server of the medical institution to obtain, for example, appointment information and a diagnosis history), and the Broker sends the appointment information and the change trend of increments together to the terminal of the user. The user confirms a selected appointment, and feeds back the selected appointment to the Broker. After receiving the information, the Broker communicates with the server of the medical institution, and sends information about the user, the heart change trend, heart images, and the like to the server of the medical institution with which an appointment is confirmed by the user.

Specifically, in this embodiment of the present disclosure, the multiple medical images may be stored according to the medical image storing method 100 according to the embodiment of the present disclosure.

FIG. 4 is a schematic flowchart of an information exchanging method 400 according to an embodiment of the present disclosure. The method is executed by a server (for example, a Broker). As shown in FIG. 4, the method 400 includes the following content:

410: Acquire increments of multiple medical images of a same region of a first object relative to a reference image.

420: Determine a change trend of the multiple medical images according to the increments of the multiple medical images relative to the reference image.

430: When the change trend of the multiple medical images exceeds a preset threshold, send first information to a terminal of the first object, where the first information is used to indicate the change trend of the multiple medical images, so that the first object makes an appointment with a medical institution according to the first information.

The first information may be the change trend of the multiple medical images, or may be information that the change trend of the multiple medical images exceeds the preset threshold. In addition, the first information may be output in a form of an examination report, and the first information may also be displayed on a screen.

440: Receive a request message sent by a server of the medical institution with which the first object makes an appointment, where the request message is used to acquire the change trend of the multiple medical images and the increments of the multiple medical images relative to the reference image.

450: Send the change trend of the multiple medical images and the increments of the multiple medical images relative to the reference image to the server of the medical institution with which the first object makes an appointment.

Therefore, according to the information exchanging method in this embodiment of the present disclosure, a change trend of multiple medical images of a same region of a first object is determined, and first information used to indicate the change trend of the multiple medical images is sent to a terminal of the first object. In this way, the first object can be reminded to make an appointment with a medical institution in time according to the change trend, and the change trend is sent to the medical institution with which the first object makes an appointment, so that the user can be reminded in time to go to the medical institution for further consultation or an examination.

In other words, when the change trend of the multiple medical images of the same region of the user exceeds the preset threshold, the Broker may send the first information to the user, to remind the user to go to a medical institution for further consultation or detection, so that the user selects a medical institution for consultation/examination. Then the medical institution selected by the user initiates a request for acquiring the change trend of the multiple medical images of the user and the multiple medical images to the Broker. After receiving the request, the Broker sends the change trend of the user and the incremental images to a server of the medical institution, and may further notify the user of the sent information.

Optionally, in another embodiment of the present disclosure, the method 400 further includes: comparing the change trend of the multiple medical images of the same region of the first object with a change trend of multiple medical images of a same region of a second object, to obtain a similarity degree between the change trends of the multiple medical images of the same regions of the first object and the second object, where the first information is further used to indicate the similarity degree between the change trends of the multiple medical images of the same regions of the first object and the second object.

Optionally, for security, before sending related information of the user to the server of the medical institution, the Broker may perform authentication on the medical institution, to determine whether the medical institution is already successfully authenticated by the Broker and whether the request corresponds to the reminding content sent by the Broker to the user, and if the authentication succeeds, the Broker sends the related information of the user to the server of the medical institution.

Specifically, in this embodiment of the present disclosure, the multiple medical images may be stored according to the medical image storing method 100 according to the embodiment of the present disclosure.

An information exchanging method according to another embodiment of the present disclosure includes: acquiring increments of multiple medical images of a same region of a first object relative to a reference image; determining a change trend of the multiple medical images according to the increments of the multiple medical images relative to the reference image; and when the change trend of the multiple medical images exceeds a preset threshold, sending first information to a server of a medical institution uploading the multiple medical images, where the first information is used to indicate the change trend of the multiple medical images.

In other words, when the change trend of the multiple medical images of the same region of the first object exceeds the preset threshold, the Broker may directly send the first information to the medical institution uploading the multiple medical images of the user, so as to remind the medical institution to actively provide consultation for the user.

The following describes the information exchanging method according to this embodiment of the present disclosure in further detail with reference to a specific example in FIG. 5.

FIG. 5 is a schematic flowchart of an information exchanging method according to another embodiment of the present disclosure. The method in FIG. 5 is a specific example of the method in FIG. 3, and detailed descriptions are properly omitted herein. As shown in FIG. 5, the method includes the following content:

501: A Broker determines a change trend of medical images of a same region of a first object according to stored increments of the medical images of the same region relative to a reference image.

502: Compare the change trend with a preset indicator threshold.

503: When the change trend exceeds the preset indicator threshold, perform 504; otherwise, perform 507.

504: Select a change trend of medical images of a relative (for example, the father or mother) of the first object.

505: Compare and analyze the change trend of the medical images of the first object and the change trend of the medical images of the relative of the first object, to obtain a similarity degree between the two.

506: The Broker selects corresponding appointment information (a department or a doctor) from a medical institution/a healthcare provider that subscribes to a service of the Broker, and sends the appointment information, the change trend of the medical images of the first object, and the similarity degree to a user terminal.

507: After receiving appointment confirmation information of the first object, the Broker communicates with a server of the medical institution selected by the first object, and sends information about the first object, the change trend of the medical images of the same region of the first object, and the increments of the medical images of the same region of the first object to the server of the medical institution, to complete appointment making.

508: Complete analysis.

Therefore, according to the information exchanging method in this embodiment of the present disclosure, increments of multiple medical images of a same region of a first object relative to a reference image are acquired, a change trend of the multiple medical images is determined, first information used to indicate the change trend of the multiple medical images is sent to a terminal of the first object, and appointment information of a medical institution is sent to the terminal of the first object. In this way, the appointment information of the medical institution can be actively pushed to the first object according to the change trend of the medical images of the same region of the first object.

Figure 6:
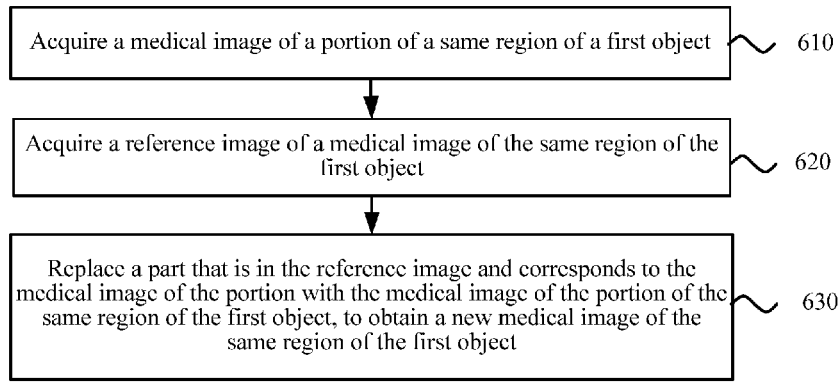
FIG. 6 is a schematic flowchart of a medical image processing method according to an embodiment of the present disclosure.

The following describes a medical image processing method according to an embodiment of the present disclosure in detail with reference to FIG. 6. For multiple photographed medical images of a same region of a first object, it is possible that only a portion of the same region changes, for example, in an application scenario of microscope-level micro-photographing, the portion may be very tiny, and in this case, other parts in the medical images of the entire same region of the first object are of low significance. Besides, resources need to be used to photograph the medical images of the entire same region of the first object, and the medical images of the entire same region need to occupy storage space.

FIG. 6 is a schematic flowchart of a medical image processing method 600 according to an embodiment of the present disclosure. The method may be executed by a medical device, or may be executed by a server (for example, a Broker), which is not limited in this embodiment of the present disclosure. As shown in FIG. 6, the method 600 includes the following content:

610: Acquire a medical image of a portion of a same region of a first object.

620: Acquire a reference image of a medical image of the same region of the first object.

630: Replace a part that is in the reference image and corresponds to the medical image of the portion with the medical image of the portion of the same region of the first object, to obtain a new medical image of the same region of the first object.

For example, currently, only a medical image of a portion of the same region of the first object changes, and in this case, only the medical image of the portion of the same region needs to be stored, and a new medical image of the same region of the first object does not need to be stored. When necessary, a part that is in the reference image and corresponds to the medical image of the portion is replaced with the medical image of the portion of the same region, to obtain the new medical image.

Therefore, according to the medical image processing method in this embodiment of the present disclosure, a medical image of a portion of a same region of a first object and a reference image of a medical image of the same region are acquired, and a part that is in the reference image and corresponds to the medical image of the portion is replaced with the medical image of the portion, to obtain a new medical image of the same region of the first object. In this way, to obtain a new medical image of the same region of the first object, only a medical image of a changed portion of the same region of the first object needs to be acquired, thereby occupying less storage space or transmission resources.

Optionally, in still another embodiment of the present disclosure, the method 600 is executed by an image collection device, and the method 600 further includes: receiving a notification message sent by a server, where the notification message is used to instruct the image collection device to photograph a medical image of the portion of the same region of the first object; and sending the new medical image of the same region of the first object to the server, where the acquiring a medical image of a portion of a same region of the first object includes: photographing the medical image of the portion of the same region of the first object.

In other words, the server determines, according to a change trend of medical images of the same region of the first object, that only a portion of the same region changes; therefore, the server sends a notification message to the image collection device, to instruct the image collection device to photograph a medical image of only the portion. After photographing a medical image of the portion according to the notification message, the image collection device may acquire a reference image of the same region from a storage unit or request a reference image of the same region from the server, then replace a part that is in the reference image and corresponds to the portion with the medical image of the portion, to obtain a new medical image of the same region, and may further send the new medical image to the server afterwards.

Optionally, in still another embodiment of the present disclosure, the method 600 is executed by a server, and the method 600 further includes: sending a notification message to an image collection device, where the notification message is used to instruct the image collection device to photograph a medical image of the portion of the same region of the first object, where the acquiring a medical image of a portion of a same region of a first object includes: receiving the medical image, which is sent by the image collection device, of the portion of the same region of the first object.

In other words, the server determines, according to a change trend of medical images of the same region of the first object, that only a portion of the same region changes; therefore, the server sends a notification message to the image collection device, to instruct the image collection device to photograph a medical image of only the portion. After photographing a medical image of the portion according to the notification message, the image collection device sends the medical image of the portion to the server. The server acquires a reference image of the same region of the first object, and replaces a part that is in the reference image and corresponds to the portion with the medical image of the portion, thereby obtaining a new medical image of the same region.

Therefore, according to the medical image processing method in this embodiment of the present disclosure, a medical image of a portion of a same region of a first object and a reference image of a medical image of the same region are acquired, and a part that is in the reference image and corresponds to the medical image of the portion is replaced with the medical image of the portion, to obtain a new medical image of the same region of the first object. In this way, to obtain a new medical image of the same region of the first object, only a medical image of a changed portion of the same region of the first object needs to be acquired, thereby occupying less storage space or transmission resources.

The foregoing describes the medical image storing method, the information exchanging method, and the medical image processing method according to the embodiments of the present disclosure in detail with reference to FIG. 1 to FIG. 6, and the following describes a medical image storing apparatus, an information exchanging apparatus, and a medical image processing apparatus according to embodiments of the present disclosure in detail with reference to FIG. 7 to FIG. 12.

Figure 7:
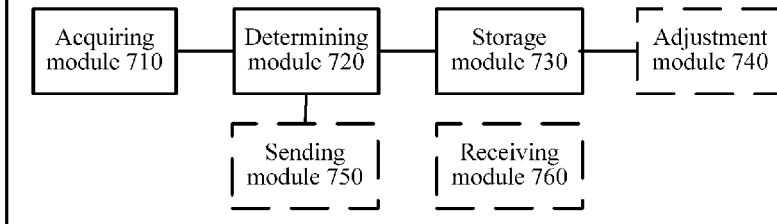
FIG. 7 is a schematic block diagram of a medical image storing apparatus according to an embodiment of the present disclosure.

FIG. 7 is a schematic block diagram of a medical image storing apparatus 700 according to an embodiment of the present disclosure. As shown in FIG. 7, the apparatus 700 includes: an acquiring module 710, a determining module 720, and a storage module 730.

The acquiring module 710 is configured to acquire a medical image and a reference image, where the medical image and the reference image are images of a same region of a first object that are photographed at different times. The determining module 720 is configured to determine an increment of the medical image relative to the reference image. The storage module 730 is configured to store the increment of the medical image relative to the reference image.

Specifically, when storing the increment of the medical image relative to the reference image, the storage module 730 may also store a correspondence between the increment and the reference image. For example, the correspondence may be stored in a header of a data packet of the increment. When the medical image corresponding to the increment needs to be viewed, the reference image corresponding to the increment is determined according to the correspondence between the increment and the reference image, and after processing is performed on the increment and the reference image, the medical image corresponding to the increment can be restored.

Because the medical image and reference image are photographed for the same region of the first object, the twos images may have a lot of same parts. Therefore, the increment may be very small, which obviously reduces requirements on storage space during storage.

Therefore, according to the medical image storing apparatus in this embodiment of the present disclosure, an increment of a medical image relative to a reference image is determined, and only the reference image and the increment of the medical image relative to the reference image are stored, thereby reducing storage space occupied by a medical image.

Specifically, in this embodiment of the present disclosure, a type of the medical image includes: magnetic resonance imaging MRI or computed tomography CT or X-ray.

Specifically, in another embodiment of the present disclosure, the determining module 720 is further configured to determine, according to a photographing time or photographing frequency, to use a medical image of the same region of the first object as the reference image.

Optionally, in another embodiment of the present disclosure, before acquiring the medical image and the reference image, the acquiring module 710 is further configured to acquire the first photographed medical image of the same region of the first object; and the determining module is further configured to use the first photographed medical image of the same region of the first object as the reference image of a subsequently photographed medical image.

In other words, when the current medical image has no reference image, the medical image is used as a reference image.

Specifically, in another embodiment of the present disclosure, the determining module 720 is specifically configured to perform residual processing or variance processing on the medical image and the reference image, to obtain the increment of the medical image relative to the reference image.

Optionally, in another embodiment of the present disclosure, the apparatus 700 further includes: an adjustment module 740 configured to adjust the medical image according to the reference image, where the determining module 720 is specifically configured to determine an increment of the adjusted medical image relative to the reference image.

Specifically, in another embodiment of the present disclosure, the apparatus 700 is an image collection device, and the acquiring module 710 is specifically configured to photograph the medical image and the reference image.

For example, the acquiring module may be a camera. The image collection device may be a terminal for home use, or may be a specialized medical photographing device of a medical institution. For example, after photographing a medical image, for medical images of a same region of a same object, the medical photographing device saves only a reference image and an increment of another medical image relative to the reference image, which can reduce storage space of the medical photographing device occupied by a medical image.

More specifically, in another embodiment of the present disclosure, the acquiring module 710 is specifically configured to successively photograph multiple medical images, where the multiple medical images include the medical image or the reference image.

Specifically, in another embodiment of the present disclosure, the acquiring module 710 photographs the medical image or the reference image by means of microscope-level micro-photographing or at millisecond-level frequency.

For example, the acquiring module 710 may be a camera, and the camera may successively photograph the medical image and the reference image at millisecond-level frequency. The reference image is a medical image among multiple medical images successively photographed by the image collection device, for example, the reference image is the first medical image among the multiple medical images that are successively photographed by the image collection device. Especially for a case in which multiple medical images of a same region of a same object need to be successively photographed, the method in this embodiment of the present disclosure can obviously reduce storage space occupied by an image. For example, because a user needs to successively photograph multiple images to observe a change in a sample within a time period, if saving each image causes shortage of storage space, using the medical image storing method in this embodiment of the present disclosure can obviously alleviate the storage problem. For another example, 10 images showing changes in cells in a blood sample are photographed at a high speed, for example, the first photographed image is selected as a reference image, after 9 increments of the remaining 9 images relative to the reference image are determined, only the reference image and the 9 increments need to be saved in a storage unit.

Optionally, in another embodiment of the present disclosure, the apparatus 700 is an image collection device, and the apparatus 700 further includes: a sending module 750 configured to send the reference image and increments of the multiple medical images relative to the reference image to a server, so that the server provides health advice information for the first object according to the reference image and the increments of the multiple medical images relative to the reference image.

The medical image storing method according to this embodiment of the present disclosure can reduce space occupied by a medical image, but the image collection device has limited storage space and cannot save, in the storage unit of the image collection device, all images that are photographed within a long time period, while the server has large storage space; therefore, the image collection device sends the reference image and the increments to the server, thereby saving the images that are photographed within a long time period.

The image collection device may not store the reference image and the increments of the multiple medical images relative to the reference image, which is not limited in this embodiment of the present disclosure.

Alternatively, in another embodiment of the present disclosure, the apparatus 700 is an image collection device, and the determining module 720 is further configured to determine a change trend of the multiple medical images according to increments of the multiple medical images relative to the reference image. The sending module 750 is further configured to send the change trend of the multiple medical images to a server, so that the server provides health advice information for the first object according to the change trend of the multiple medical images.

Optionally, in another embodiment of the present disclosure, the apparatus 700 further includes a receiving module 760 configured to receive a message sent by the server, where the message is health advice for the first object.

Optionally, in another embodiment of the present disclosure, the apparatus 700 may further send the reference image and the increments of the multiple images relative to the reference image to a medical institution selected by a user for an appointment, or send the change trend of the multiple medical images to a medical institution selected by a user for an appointment, so that the medical institution selected by the user for an appointment uses the reference image and the increments or the change trend as a reference for diagnosis.

Specifically, in another embodiment of the present disclosure, the apparatus 700 is a server, and the acquiring module 710 is specifically configured to receive the medical image by using a network, and acquire the reference image from a database.

Specifically, in another embodiment of the present disclosure, the acquiring module 710 is specifically configured to receive a data packet of the medical image by using the network, where the data packet includes the medical image, an identity ID of the first object, and information indicating the same region.

The data packet may further include information such as a photographing date of the medical image and a type of the medical image, which is not limited in this embodiment of the present disclosure.

It should be understood that the medical image storing apparatus 700 according to this embodiment of the present disclosure may correspond to the server or the image collection device in the medical image storing method 100 according to the embodiment of the present disclosure, and the foregoing and other operations and/or functions of the modules in the apparatus 700 are separately for implementing corresponding procedures in the medical image storing method according to the embodiment of the present disclosure. For brevity, details are not described herein.

Therefore, according to the medical image storing apparatus in this embodiment of the present disclosure, an increment of a medical image relative to a reference image is determined, and only the reference image and the increment of the medical image relative to the reference image are stored, thereby reducing storage space occupied by a medical image.

Figure 8:
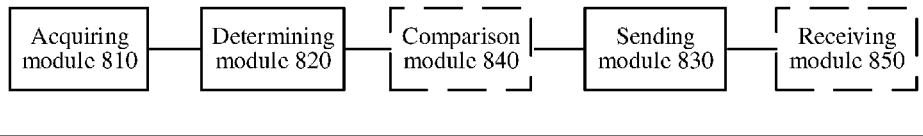
FIG. 8 is a schematic block diagram of an information exchanging apparatus according to an embodiment of the present disclosure.

FIG. 8 is a schematic block diagram of an information exchanging apparatus 800 according to an embodiment of the present disclosure. As shown in FIG. 8, the apparatus 800 includes: an acquiring module 810, a determining module 820, and a sending module 830.

The acquiring module 810 is configured to acquire increments of multiple medical images of a same region of a first object relative to a reference image. The determining module 820 is configured to determine a change trend of the multiple medical images according to the increments of the multiple medical images relative to the reference image. The sending module 830 is configured to: when the change trend of the multiple medical images exceeds a preset threshold, send first information to a terminal of the first object, where the first information is used to indicate the change trend of the multiple medical images, and send appointment information of a medical institution to the terminal of the first object, where the appointment information is used to indicate an available medical resource of the medical institution.

In other words, when the change trend of the multiple medical images of the same region of the first object exceeds the preset threshold, a Broker may actively push information about an available medical institution to the first object. Specifically, when determining to push information about an available medical institution to the first object, the Broker may determine a corresponding available department and medical institution according to the region, whose change trend exceeds the preset threshold, of the first object, and may further determine preferred appointment information according to information about the first object. For example, a medical institution closer to the first object may be further determined according to an address of the first object.

Therefore, according to the information exchanging apparatus in this embodiment of the present disclosure, increments of multiple medical images of a same region of a first object relative to a reference image are acquired, a change trend of the multiple medical images is determined, first information used to indicate the change trend of the multiple medical images is sent to the first object, and appointment information of a medical institution is sent to the first object. In this way, the appointment information of the medical institution can be actively pushed to the first object according to the change trend of the medical images of the same region of the first object.

Optionally, in another embodiment of the present disclosure, before sending the appointment information of the medical institution to the terminal of the first object, the sending module 300 is further configured to: establish communication with a server of the medical institution, and acquire the appointment information of the medical institution, where the appointment information includes the following information: a department, a time, and a doctor.

Optionally, in another embodiment of the present disclosure, the apparatus 800 further includes: a comparison module 840 configured to compare the change trend of the multiple medical images of the same region of the first object with a change trend of multiple medical images of a same region of a second object, to obtain a similarity degree between the change trends of the multiple medical images of the same regions of the first object and the second object, where the first information is further used to indicate the similarity degree between the change trends of the multiple medical images of the same regions of the first object and the second object.

Optionally, in another embodiment of the present disclosure, the apparatus 800 further includes: a receiving module 850 configured to receive appointment confirmation information sent by the terminal of the first object, where the sending module 830 is further configured to send, according to the appointment confirmation information, the change trend of the multiple medical images and the increments of the multiple medical images relative to the reference image to the server of the medical institution confirmed by the first object.

In other words, when the change trend of the multiple medical images of the same region of the first object exceeds the preset threshold, or when the similarity degree between the change trends of the multiple medical images of the same regions of the first object and the second object exceeds the preset threshold, the Broker may actively recommend information about an available medical institution to the first object.

Specifically, in this embodiment of the present disclosure, the multiple medical images may be stored by the medical image storing apparatus 700 according to the embodiment of the present disclosure.

It should be understood that the information exchanging apparatus 800 according to this embodiment of the present disclosure may correspond to the server in the information exchanging method 300 according to the embodiment of the present disclosure, and the foregoing and other operations and/or functions of the modules in the apparatus 800 are separately for implementing corresponding procedures in the information exchanging method according to the embodiment of the present disclosure. For brevity, details are not described herein.

Therefore, according to the information exchanging apparatus in this embodiment of the present disclosure, increments of multiple medical images of a same region of a first object relative to a reference image are acquired, a change trend of the multiple medical images is determined, first information used to indicate that the change trend of the multiple medical images exceeds a preset threshold is sent to the first object, and appointment information of a medical institution is sent to the first object. In this way, the appointment information of the related medical institution can be actively pushed to the first object according to the change trend of the medical images of the same region of the first object.

Figure 9:
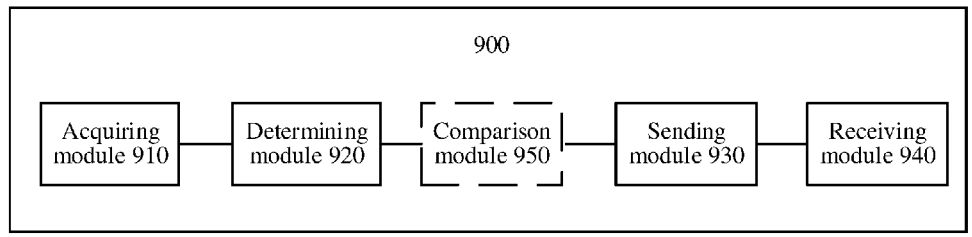
FIG. 9 is a schematic block diagram of an information exchanging apparatus according to another embodiment of the present disclosure.

FIG. 9 is a schematic block diagram of an information exchanging apparatus 900 according to another embodiment of the present disclosure. The method is executed by a server (for example, a Broker). As shown in FIG. 9, the information exchanging apparatus 900 includes the following content: an acquiring module 910 configured to acquire increments of multiple medical images of a same region of a first object relative to a reference image; a determining module 920 configured to determine a change trend of the multiple medical images according to the increments of the multiple medical images relative to the reference image; a sending module 930 configured to: when the change trend of the multiple medical images exceeds a preset threshold, send first information to a terminal of the first object, where the first information is used to indicate the change trend of the multiple medical images, so that the first object makes an appointment with a medical institution according to the first information; and a receiving module 940 configured to receive a request message sent by a server of the medical institution with which the first object makes an appointment, where the request message is used to acquire the change trend of the multiple medical images and the increments of the multiple medical images relative to the reference image, where the sending module 930 is further configured to send the change trend of the multiple medical images and the increments of the multiple medical images relative to the reference image to the server of the medical institution with which the first object makes an appointment.

Therefore, according to the information exchanging apparatus in this embodiment of the present disclosure, a change trend of multiple medical images of a same region of a first object is determined, and first information used to indicate that the change trend of the multiple medical images exceeds a preset threshold is sent to the first object. In this way, the first object can be reminded to make an appointment with a medical institution in time according to the change trend, and the change trend is sent to the medical institution with which the first object makes an appointment, so that the user can be reminded in time to go to the medical institution for further consultation or an examination.

Optionally, in another embodiment of the present disclosure, the apparatus 900 further includes: a comparison module 950 configured to compare the change trend of the multiple medical images of the same region of the first object with a change trend of multiple medical images of a same region of a second object, to obtain a similarity degree between the change trends of the multiple medical images of the same regions of the first object and the second object, where the first information is further used to indicate the similarity degree between the change trends of the multiple medical images of the same regions of the first object and the second object.

Optionally, for security, before sending related information of the user to the server of the medical institution, the Broker may perform authentication on the medical institution, to determine whether the medical institution is already successfully authenticated by the Broker and whether the request corresponds to the reminding content sent by the Broker to the user, and if the authentication succeeds, the Broker sends the related information of the user to the server of the medical institution.

Specifically, in this embodiment of the present disclosure, the multiple medical images may be stored by the medical image storing apparatus 700 according to the embodiment of the present disclosure.

It should be understood that the information exchanging apparatus 900 according to this embodiment of the present disclosure may correspond to the server in the information exchanging method 400 according to the embodiment of the present disclosure, and the foregoing and other operations and/or functions of the modules in the apparatus 900 are separately for implementing corresponding procedures in the information exchanging method according to the embodiment of the present disclosure. For brevity, details are not described herein.

Therefore, according to the information exchanging apparatus in this embodiment of the present disclosure, a change trend of multiple medical images of a same region of a first object is determined, and first information used to indicate that the change trend of the multiple medical images exceeds a preset threshold is sent to the first object. In this way, the first object can be reminded to make an appointment with a medical institution in time according to the change trend, and the change trend is sent to the medical institution with which the first object makes an appointment, so that the user can be reminded in time to go to the medical institution for further consultation or an examination.

An information exchanging apparatus according to another embodiment of the present disclosure includes: an acquiring module configured to acquire increments of multiple medical images of a same region of a first object relative to a reference image; a determining module configured to determine a change trend of the multiple medical images according to the increments of the multiple medical images relative to the reference image; and a sending module configured to: when the change trend of the multiple medical images exceeds a preset threshold, send the first information to a server of a medical institution uploading the multiple medical images, where the first information is used to indicate that the change trend of the multiple medical images exceeds the preset threshold.

In other words, when the change trend of the multiple medical images of the same region of the first object exceeds the preset threshold, or when the similarity degree between the change trends of the multiple medical images of the same regions of the first object and the second object exceeds the preset threshold, the Broker may directly send the first information to the medical institution uploading the multiple medical images of the user, so as to remind the medical institution to actively provide consultation for the user.

Figure 10:
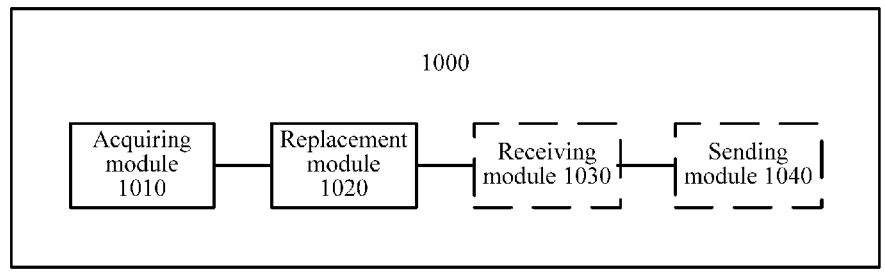
FIG. 10 is a schematic block diagram of a medical image processing apparatus according to an embodiment of the present disclosure.

FIG. 10 is a schematic block diagram of a medical image processing apparatus 1000 according to an embodiment of the present disclosure. As shown in FIG. 10, the apparatus 1000 includes: an acquiring module 1010 and a replacement module 1020.

The acquiring module 1010 is configured to acquire a medical image of a portion of a same region of a first object. The acquiring module 1010 is further configured to acquire a reference image of a medical image of the same region of the first object. The replacement module 1020 is configured to replace a part that is in the reference image and corresponds to the medical image of the portion with the medical image of the portion of the same region of the first object, to obtain a new medical image of the same region of the first object.

Therefore, according to the medical image processing apparatus in this embodiment of the present disclosure, a medical image of a portion of a same region of a first object and a reference image of a medical image of the same region are acquired, and a part that is in the reference image and corresponds to the medical image of the portion is replaced with the medical image of the portion, to obtain a new medical image of the same region of the first object. In this way, to obtain a new medical image of the same region of the first object, only a medical image of a changed portion of the same region of the first object needs to be acquired, thereby occupying less storage space or transmission resources.

Optionally, in another embodiment of the present disclosure, the apparatus 1000 is an image collection device, and the apparatus 1000 further includes: a receiving module 1030 configured to receive a notification message sent by a server, where the notification message is used to instruct the image collection device to photograph a medical image of the portion of the same region of the first object; and a sending module 1040 configured to send the new medical image of the same region of the first object to the server, where the acquiring module 1010 is further configured to photograph the medical image of the portion of the same region of the first object.

In other words, the server determines, according to a change trend of medical images of the same region of the first object, that only a portion of the same region changes; therefore, the server sends a notification message to the image collection device, to instruct the image collection device to photograph a medical image of only the portion. After photographing a medical image of the portion according to the notification message, the image collection device may acquire a reference image of the same region from a storage unit or request a reference image of the same region from the server, then replace a part that is in the reference image and corresponds to the portion with the medical image of the portion, to obtain a new medical image of the same region, and may further send the new medical image to the server afterwards.

Optionally, in another embodiment of the present disclosure, the apparatus 1000 is a server, and the sending module 1040 is configured to send a notification message to an image collection device, where the notification message is used to instruct the image collection device to photograph a medical image of the portion of the same region of the first object, where the acquiring module 1010 is specifically configured to receive the medical image, which is sent by the image collection device, of the portion of the same region of the first object.

In other words, the server determines, according to a change trend of medical images of the same region of the first object, that only a portion of the same region changes; therefore, the server sends a notification message to the image collection device, to instruct the image collection device to photograph a medical image of only the portion. After photographing a medical image of the portion according to the notification message, the image collection device sends the medical image of the portion to the server. The server acquires a reference image of the same region of the first object, and replaces a part that is in the reference image and corresponds to the portion with the medical image of the portion, thereby obtaining a new medical image of the same region.

It should be understood that the medical image processing apparatus 1000 according to this embodiment of the present disclosure may correspond to the server or the image collection device in the medical image processing method 600 according to the embodiment of the present disclosure, and the foregoing and other operations and/or functions of the modules in the apparatus 1000 are separately for implementing corresponding procedures in the medical image processing method according to the embodiment of the present disclosure. For brevity, details are not described herein.

Therefore, according to the medical image processing apparatus in this embodiment of the present disclosure, a medical image of a portion of a same region of a first object and a reference image of a medical image of the same region are acquired, and a part that is in the reference image and corresponds to the medical image of the portion is replaced with the medical image of the portion, to obtain a new medical image of the same region of the first object. In this way, to obtain a new medical image of the same region of the first object, only a medical image of a changed portion of the same region of the first object needs to be acquired, thereby occupying less storage space or transmission resources.

Figure 11:
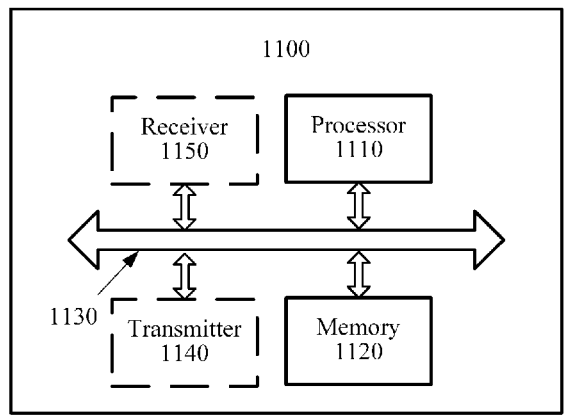
FIG. 11 is a schematic block diagram of a medical image storing apparatus according to another embodiment of the present disclosure.

FIG. 11 is a schematic block diagram of a medical image storing apparatus 1100 according to another embodiment of the present disclosure. As shown in FIG. 11, the terminal device 1100 includes a processor 1110, a memory 1120, and a bus system 1130. The processor 1110 and the memory 1120 are connected to each other by using the bus system 1130, the memory 1120 is configured to store an instruction, and the processor 1110 is configured to execute the instruction stored in the memory 1120.

The processor 1110 is configured to acquire a medical image and a reference image, where the medical image and the reference image are images of a same region of a first object that are photographed at different times, and determine an increment of the medical image relative to the reference image. The memory 1120 is configured to store the increment of the medical image relative to the reference image.

Therefore, according to the medical image storing apparatus in this embodiment of the present disclosure, an increment of a medical image relative to a reference image is determined, and only the reference image and the increment of the medical image relative to the reference image are stored, thereby reducing storage space occupied by a medical image.

It should be understood that in this embodiment of the present disclosure, the processor 1110 may be a central processing unit (CPU), or the processor 1110 may be another general purpose processor, digital signal processor (DSP), application-specific integrated circuit (ASIC), or field-programmable gate array (FPGA), or another programmable logic device, discrete gate or transistor logic device, independent hardware component, or the like. The general purpose processor may be a microprocessor, or the processor may be any conventional processor or the like.

The memory 1120 may include a read-only memory and a random access memory, and provide an instruction and data to the processor 1110. The memory 1120 may further include a nonvolatile random access memory. For example, the memory 1120 may further store information about a device type.

The bus system 1130, besides including a data bus, may further include a power bus, a control bus, a status signal bus, and the like. However, for a purpose of a clear explanation, all buses are marked as the bus system 1130 in the figure.

In an implementation process, each step of the method may be completed by using an integrated logic circuit of hardware in the processor 1110 or instructions in a software form. The steps of the foregoing method disclosed with reference to the embodiments of the present disclosure may be directly performed by a hardware processor, or may be performed by using a combination of hardware in the processor and a software module. The software module may be located in a mature storage medium in the art, such as a random access memory, a flash memory, a read-only memory, a programmable read-only memory, an electronically erasable programmable memory, or a register. The storage medium is located in the memory 1120, and the processor 1110 reads information in the memory 1120, and completes the steps of the method in combination with the hardware thereof. To avoid repetition, details are not described herein.

Specifically, in this embodiment of the present disclosure, a type of the medical image includes: magnetic resonance imaging MRI or computed tomography CT or X-ray.

Specifically, in another embodiment of the present disclosure, the processor 1110 is further configured to determine, according to a photographing time or photographing frequency, to use a medical image of the same region of the first object as the reference image.

Optionally, in another embodiment of the present disclosure, before acquiring the medical image and the reference image, the processor 1110 is further configured to acquire the first photographed medical image of the same region of the first object; and use the first photographed medical image of the same region of the first object as the reference image of a subsequently photographed medical image.

Specifically, in another embodiment of the present disclosure, the processor 1110 is specifically configured to perform residual processing or variance processing on the medical image and the reference image, to obtain the increment of the medical image relative to the reference image.

Optionally, in another embodiment of the present disclosure, the processor 1110 is further configured to adjust the medical image according to the reference image, and determine an increment of the adjusted medical image relative to the reference image.

Specifically, in another embodiment of the present disclosure, the apparatus 1100 is an image collection device, the image collection device further includes a camera, and the processor 1110 is further configured to control the camera to photograph the medical image and the reference image.

More specifically, in another embodiment of the present disclosure, the processor 1110 is further configured to control the camera to successively photograph multiple medical images, where the multiple medical images include the medical image or the reference image.

Specifically, in another embodiment of the present disclosure, the processor 1110 is further configured to control the camera to photograph the medical image or the reference image by means of microscope-level micro-photographing or at millisecond-level frequency.

Optionally, in another embodiment of the present disclosure, the apparatus 1100 is an image collection device, and the apparatus 1100 further includes: a transmitter 1140 configured to send the reference image and increments of the multiple medical images relative to the reference image to a server, so that the server provides health advice information for the first object according to the reference image and the increments of the multiple medical images relative to the reference image.

The storage unit of the image collection device may not store the reference image and the increments of the multiple medical images relative to the reference image, which is not limited in this embodiment of the present disclosure.

Alternatively, in another embodiment of the present disclosure, the apparatus 1100 is an image collection device, and the processor 1110 is further configured to determine a change trend of the multiple medical images according to increments of the multiple medical images relative to the reference image. The transmitter 1140 is further configured to send the change trend of the multiple medical images to a server, so that the server provides health advice information for the first object according to the change trend of the multiple medical images.

Optionally, in another embodiment of the present disclosure, the apparatus 1100 further includes a receiver 1150 configured to receive a message sent by the server, where the message is health advice for the first object.

Optionally, in another embodiment of the present disclosure, the apparatus 1100 is a server, the receiver 1150 is specifically configured to receive the medical image by using a network, and the processor 1110 is specifically configured to acquire the reference image from a database.

Specifically, in another embodiment of the present disclosure, the processor 1110 is specifically configured to receive a data packet of the medical image by using the network, where the data packet includes the medical image, an ID of the first object, and information indicating the same region.

The data packet may further include information such as a photographing date of the medical image and a type of the medical image, which is not limited in this embodiment of the present disclosure.

It should be understood that the medical image storing apparatus 1100 according to this embodiment of the present disclosure may correspond to the server or the image collection device in the medical image storing method 100 according to the embodiment of the present disclosure and the medical image storing apparatus 700 according to the embodiment of the present disclosure, and the foregoing and other operations and/or functions of the modules in the apparatus 1100 are separately for implementing corresponding procedures in the medical image storing method according to the embodiment of the present disclosure. For brevity, details are not described herein.

Therefore, according to the medical image storing apparatus in this embodiment of the present disclosure, an increment of a medical image relative to a reference image is determined, and only the reference image and the increment of the medical image relative to the reference image are stored, thereby reducing storage space occupied by a medical image.

Figure 12:
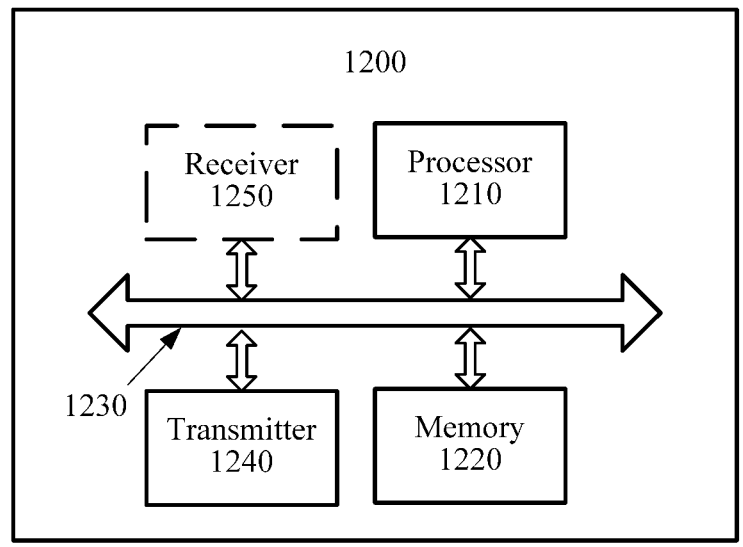
FIG. 12 is a schematic block diagram of an information exchanging apparatus according to another embodiment of the present disclosure.

FIG. 12 is a schematic block diagram of an information exchanging apparatus 1200 according to another embodiment of the present disclosure. As shown in FIG. 12, the apparatus 1200 includes: a processor 1210, a memory 1220, a bus system 1230, a receiver 1250 and a transmitter 1240. The processor 1210, the memory 1220, and the transmitter 1240 are connected to each other by using the bus system 1230, the memory 1220 is configured to store an instruction, and the processor 1210 is configured to execute the instruction stored in the memory 1220.

The processor 1210 is configured to acquire increments of multiple medical images of a same region of a first object relative to a reference image. The processor 1210 is further configured to determine a change trend of the multiple medical images according to the increments of the multiple medical images relative to the reference image. The transmitter 1240 is configured to: when the change trend of the multiple medical images exceeds a preset threshold, send first information to a terminal of the first object, where the first information is used to indicate the change trend of the multiple medical images, and send appointment information of a medical institution to the terminal of the first object, where the appointment information is used to indicate an available medical resource of the medical institution.

Therefore, according to the information exchanging apparatus in this embodiment of the present disclosure, increments of multiple medical images of a same region of a first object relative to a reference image are acquired, a change trend of the multiple medical images is determined, first information used to indicate the change trend of the multiple medical images is sent to a terminal of the first object, and appointment information of a medical institution is sent to the terminal of the first object. In this way, the appointment information of the related medical institution can be actively pushed to the first object according to the change trend of the medical images of the same region of the first object.

It should be understood that in this embodiment of the present disclosure, the processor 1210 may be a CPU or the processor 1210 may be another general purpose processor, DSP, ASIC, or FPGA, or another programmable logic device, discrete gate or transistor logic device, independent hardware component, or the like. The general purpose processor may be a microprocessor, or the processor may be any conventional processor or the like.

The memory 1220 may include a read-only memory and a random access memory, and provide an instruction and data to the processor 1210. The memory 1220 may further include a nonvolatile random access memory. For example, the memory 1220 may further store information about a device type.

The bus system 1230, besides including a data bus, may further include a power bus, a control bus, a status signal bus, and the like. However, for a purpose of a clear explanation, all buses are marked as the bus system 1230 in the figure.

In an implementation process, each step of the method may be completed by using an integrated logic circuit of hardware in the processor 1210 or instructions in a software form. The steps of the foregoing method disclosed with reference to the embodiments of the present disclosure may be directly performed by a hardware processor, or may be performed by using a combination of hardware in the processor and a software module. The software module may be located in a mature storage medium in the art, such as a random access memory, a flash memory, a read-only memory, a programmable read-only memory, an electronically erasable programmable memory, or a register. The storage medium is located in the memory 1220, and the processor 1210 reads information in the memory 1220, and completes the steps of the method in combination with the hardware thereof. To avoid repetition, details are not described herein.

Optionally, in another embodiment of the present disclosure, the processor 1110 is further configured to compare the change trend of the multiple medical images of the same region of the first object with a change trend of multiple medical images of a same region of a second object, to obtain a similarity degree between the change trends of the multiple medical images of the same regions of the first object and the second object, where the first information is used to indicate the similarity degree between the change trends of the multiple medical images of the same regions of the first object and the second object.

Optionally, in another embodiment of the present disclosure, the apparatus 1100 further includes: a receiver 1150 configured to receive appointment confirmation information sent by the terminal of the first object, where the transmitter 1140 is further configured to send, according to the appointment confirmation information, the change trend of the multiple medical images and the increments of the multiple medical images relative to the reference image to the server of the medical institution confirmed by the first object.

Specifically, in this embodiment of the present disclosure, the multiple medical images may be stored by the medical image storing apparatus 700 or the apparatus 1100 according to the embodiment of the present disclosure.

It should be understood that the information exchanging apparatus 1200 according to this embodiment of the present disclosure may correspond to the server in the information exchanging method 300 according to the embodiment of the present disclosure, and the foregoing and other operations and/or functions of the modules in the apparatus 1200 are separately for implementing corresponding procedures in the information exchanging method according to the embodiment of the present disclosure. For brevity, details are not described herein.

Therefore, according to the information exchanging apparatus in this embodiment of the present disclosure, increments of multiple medical images of a same region of a first object relative to a reference image are acquired, a change trend of the multiple medical images is determined, first information used to indicate that the change trend of the multiple medical images exceeds a preset threshold is sent to a terminal of the first object, and appointment information of a medical institution is sent to the terminal of the first object. In this way, the appointment information of the related medical institution can be actively pushed to the first object according to the change trend of the medical images of the same region of the first object.

Figure 13:
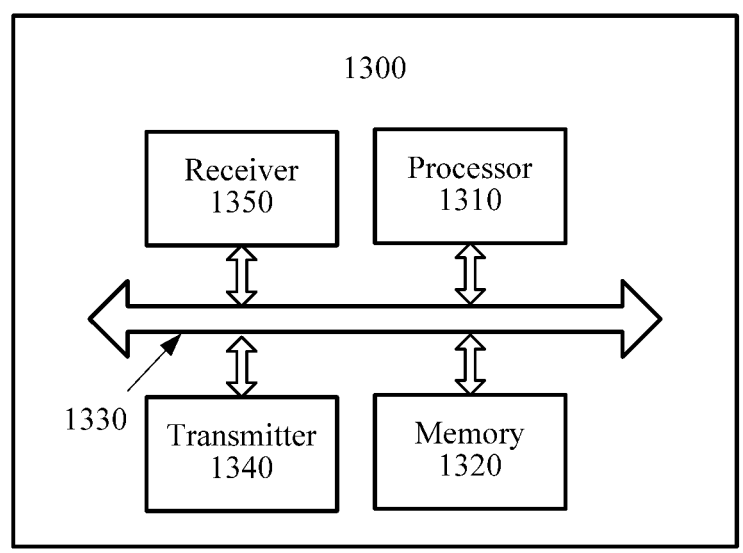
FIG. 13 is a schematic block diagram of an information exchanging apparatus according to another embodiment of the present disclosure.

FIG. 13 is a schematic block diagram of an information exchanging apparatus 1300 according to another embodiment of the present disclosure. As shown in FIG. 13, the apparatus 1300 includes: a processor 1310, a memory 1320, a bus system 1330, a transmitter 1340, and a receiver 1350. The processor 1310, the memory 1320, the transmitter 1340, and the receiver 1350 are connected to each other by using the bus system 1330, the memory 1320 is configured to store an instruction, and the processor 1310 is configured to execute the instruction stored in the memory 1320.

The processor 1310 is configured to acquire increments of multiple medical images of a same region of a first object relative to a reference image. The processor 1310 is further configured to determine a change trend of the multiple medical images according to the increments of the multiple medical images relative to the reference image. The transmitter 1340 is configured to: when the change trend of the multiple medical images exceeds a preset threshold, send first information to a terminal of the first object, where the first information is used to indicate the change trend of the multiple medical images, so that the first object makes an appointment with a medical institution according to the first information. The receiver 1350 is configured to receive a request message sent by a server of the medical institution with which the first object makes an appointment, where the request message is used to acquire the change trend of the multiple medical images and the increments of the multiple medical images relative to the reference image. The transmitter 1340 is further configured to send the change trend of the multiple medical images and the increments of the multiple medical images relative to the reference image to the server of the medical institution with which the first object makes an appointment.

Therefore, according to the information exchanging apparatus in this embodiment of the present disclosure, a change trend of multiple medical images of a same region of a first object is determined, and first information used to indicate that the change trend of the multiple medical images exceeds a preset threshold is sent to a terminal of the first object. In this way, the first object can be reminded to make an appointment with a medical institution in time according to the change trend, and the change trend is sent to the medical institution with which the first object makes an appointment, so that the user can be reminded in time to go to the medical institution for further consultation or an examination.

Optionally, in another embodiment of the present disclosure, the processor 1310 is further configured to compare the change trend of the multiple medical images of the same region of the first object with a change trend of multiple medical images of a same region of a second object, to obtain a similarity degree between the change trends of the multiple medical images of the same regions of the first object and the second object, where the first information is further used to indicate the similarity degree between the change trends of the multiple medical images of the same regions of the first object and the second object.

Optionally, for security, before sending related information of the user to the server of the medical institution, a Broker may perform authentication on the medical institution, to determine whether the medical institution is already successfully authenticated by the Broker and whether the request corresponds to the reminding content sent by the Broker to the user, and if the authentication succeeds, the Broker sends the related information of the user to the server of the medical institution.

Specifically, in this embodiment of the present disclosure, the multiple medical images may be stored by the medical image storing apparatus 700 or the apparatus 1100 according to the embodiment of the present disclosure.

It should be understood that the information exchanging apparatus 1300 according to this embodiment of the present disclosure may correspond to the server in the information exchanging method 400 according to the embodiment of the present disclosure, and the foregoing and other operations and/or functions of the modules in the apparatus 1300 are separately for implementing corresponding procedures in the information exchanging method according to the embodiment of the present disclosure. For brevity, details are not described herein.

Therefore, according to the information exchanging apparatus in this embodiment of the present disclosure, a change trend of multiple medical images of a same region of a first object is determined, and first information used to indicate that the change trend of the multiple medical images exceeds a preset threshold is sent to a terminal of the first object. In this way, the first object can be reminded to make an appointment with a medical institution in time according to the change trend, and the change trend is sent to the medical institution with which the first object makes an appointment, so that the user can be reminded in time to go to the medical institution for further consultation or an examination.

Figure 14:
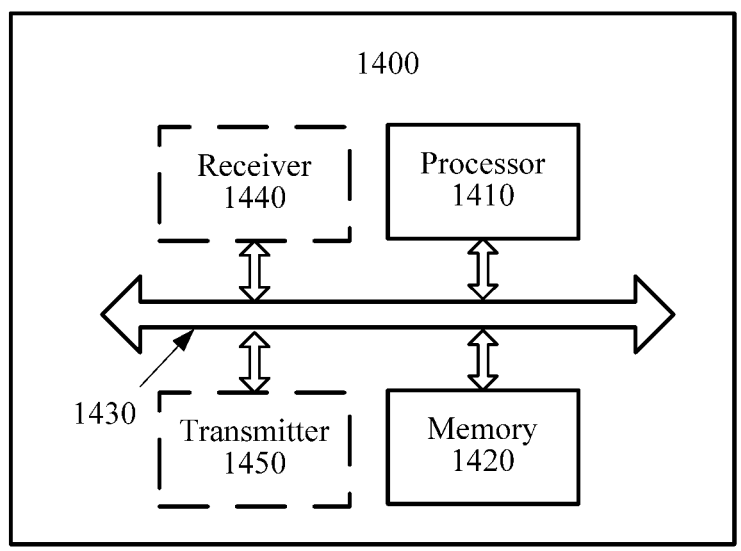
FIG. 14 is a schematic block diagram of a medical image processing apparatus according to another embodiment of the present disclosure.

FIG. 14 is a schematic block diagram of a medical image processing apparatus 1400 according to another embodiment of the present disclosure. As shown in FIG. 14, the apparatus 1400 includes a processor 1410, a memory 1420, and a bus system 1430. The processor 1410 and the memory 1420 are connected to each other by using the bus system 1430, the memory 1420 is configured to store an instruction, and the processor 1410 is configured to execute the instruction stored in the memory 1420.

The processor 1410 is configured to acquire a medical image of a portion of a same region of a first object. The processor 1410 is further configured to acquire a reference image of a medical image of the same region of the first object. The processor 1410 is further configured to replace a part that is in the reference image and corresponds to the medical image of the portion with the medical image of the portion of the same region of the first object, to obtain a new medical image of the same region of the first object.

Therefore, according to the medical image processing apparatus in this embodiment of the present disclosure, a medical image of a portion of a same region of a first object and a reference image of a medical image of the same region are acquired, and a part that is in the reference image and corresponds to the medical image of the portion is replaced with the medical image of the portion, to obtain a new medical image of the same region of the first object. In this way, to obtain a new medical image of the same region of the first object, only a medical image of a changed portion of the same region of the first object needs to be acquired, thereby occupying less storage space or transmission resources.

It should be understood that in this embodiment of the present disclosure, the processor 1410 may be a CPU, or the processor 1410 may be another general purpose processor, DSP, ASIC, or FPGA, or another programmable logic device, discrete gate or transistor logic device, independent hardware component, or the like. The general purpose processor may be a microprocessor, or the processor may be any conventional processor or the like.

The memory 1420 may include a read-only memory and a random access memory, and provide an instruction and data to the processor 1410. The memory 1420 may further include a nonvolatile random access memory. For example, the memory 1420 may further store information about a device type.

The bus system 1430, besides including a data bus, may further include a power bus, a control bus, a status signal bus, and the like. However, for a purpose of a clear explanation, all buses are marked as the bus system 1430 in the figure.

In an implementation process, each step of the method may be completed by using an integrated logic circuit of hardware in the processor 1410 or instructions in a software form. The steps of the foregoing method disclosed with reference to the embodiments of the present disclosure may be directly performed by a hardware processor, or may be performed by using a combination of hardware in the processor and a software module. The software module may be located in a mature storage medium in the art, such as a random access memory, a flash memory, a read-only memory, a programmable read-only memory, an electronically erasable programmable memory, or a register. The storage medium is located in the memory 1420, and the processor 1410 reads information in the memory 1420, and completes the steps of the method in combination with the hardware thereof. To avoid repetition, details are not described herein.

Optionally, in another embodiment of the present disclosure, the apparatus 1400 is an image collection device, and the apparatus 1400 further includes: a receiver 1440 configured to receive a notification message sent by a server, where the notification message is used to instruct the image collection device to photograph a medical image of the portion of the same region of the first object; a transmitter 1450 configured to send the new medical image of the same region of the first object to the server; and a camera configured to photograph the medical image of the portion of the same region of the first object.

Optionally, in another embodiment of the present disclosure, the apparatus 1400 is a server, and the transmitter 1450 is configured to send a notification message to an image collection device, where the notification message is used to instruct the image collection device to photograph a medical image of the portion of the same region of the first object, where the processor 1410 is specifically configured to receive the medical image, which is sent by the image collection device, of the portion of the same region of the first object.

It should be understood that the medical image processing apparatus 1400 according to this embodiment of the present disclosure may correspond to the server or the image collection device in the medical image processing method 300 according to the embodiment of the present disclosure and the medical image processing apparatus 800 according to the embodiment of the present disclosure, and the foregoing and other operations and/or functions of the modules in the apparatus 1400 are separately for implementing corresponding procedures in the medical image processing method according to the embodiment of the present disclosure. For brevity, details are not described herein.

Therefore, according to the medical image processing apparatus in this embodiment of the present disclosure, a medical image of a portion of a same region of a first object and a reference image of a medical image of the same region are acquired, and a part that is in the reference image and corresponds to the medical image of the portion is replaced with the medical image of the portion, to obtain a new medical image of the same region of the first object. In this way, to obtain a new medical image of the same region of the first object, only a medical image of a changed portion of the same region of the first object needs to be acquired, thereby occupying less storage space or transmission resources.

A person of ordinary skill in the art may be aware that, in combination with the examples described in the embodiments disclosed in this specification, units and algorithm steps may be implemented by electronic hardware or a combination of computer software and electronic hardware. Whether the functions are performed by hardware or software depends on particular applications and design constraint conditions of the technical solutions. A person skilled in the art may use different methods to implement the described functions for each particular application, but it should not be considered that the implementation goes beyond the scope of the present disclosure.

It may be clearly understood by a person skilled in the art that, for the purpose of convenient and brief description, for a detailed working process of the foregoing system, apparatus, and unit, reference may be made to a corresponding process in the foregoing method embodiments, and details are not described herein again.

In the several embodiments provided in the present application, it should be understood that the disclosed system, apparatus, and method may be implemented in other manners. For example, the described apparatus embodiment is merely exemplary. For example, the unit division is merely logical function division and may be other division in actual implementation. For example, a plurality of units or components may be combined or integrated into another system, or some features may be ignored or not performed. In addition, the displayed or discussed mutual couplings or direct couplings or communication connections may be implemented through some interfaces. The indirect couplings or communication connections between the apparatuses or units may be implemented in electronic, mechanical, or other forms.

The units described as separate parts may or may not be physically separate, and parts displayed as units may or may not be physical units, may be located in one position, or may be distributed on a plurality of network units. Some or all of the units may be selected according to actual needs to achieve the objectives of the solutions of the embodiments.

In addition, functional units in the embodiments of the present disclosure may be integrated into one processing unit, or each of the units may exist alone physically, or two or more units are integrated into one unit.

When the functions are implemented in the form of a software functional unit and sold or used as an independent product, the functions may be stored in a computer-readable storage medium. Based on such an understanding, the technical solutions of the present disclosure essentially, or the part contributing to other approaches, or some of the technical solutions may be implemented in a form of a software product. The software product is stored in a storage medium, and includes several instructions for instructing a computer device (which may be a personal computer, a server, or a network device) to perform all or some of the steps of the methods described in the embodiments of the present disclosure. The foregoing storage medium includes: any medium that can store program code, such as a Universal Serial Bus (USB) flash drive, a removable hard disk, a read-only memory (ROM), a random-access memory (RAM), a magnetic disk, or an optical disc.

What is claimed is:

1. A method, comprising:
   determining, by a processor, incremental images of first medical images of a same region of a first object relative to a reference image, wherein each of the incremental images corresponds to a respective medical image of the first medical images, wherein each of the incremental images represents one or more determined differences between the reference image and a medical image corresponding to the incremental image, and wherein a storage space required to store the incremental images is less than a storage space required to store the first medical images;
   determining, by the processor, a first change trend of the medical images according to the incremental images, wherein the first change trend indicates a trend regarding one or more changes in the first object;
   comparing, by the processor, the first change trend with a second change trend of second medical images of a region of a second object that corresponds to the first region to obtain a similarity degree between the first change trend and the second change trend;
   sending first information to a terminal of the first object when the first change trend exceeds a preset threshold, wherein the first information indicates the first change trend and the similarity degree; and
   sending appointment information of a medical institution to the terminal, wherein the appointment information indicates an available medical resource of the medical institution.

2. The method of claim 1, wherein before sending the appointment information the method further comprises:
   establishing communication with a server of the medical institution; and
   acquiring the appointment information, and
   wherein the appointment information identifies a department, a time, and a doctor.

3. The method of claim 2, further comprising:
   receiving appointment confirmation information from the terminal; and
   sending, according to the appointment confirmation information, the first change trend and the incremental images to the server.

4. The method according to claim 1, wherein determining the incremental images includes performing residual processing or variance processing relative to the reference image.

5. The method according to claim 1, wherein the incremental images include a first incremental image of one of the first medical images, and wherein before determining the incremental images, the method further includes adjusting the one of the first medical images according to the reference image.

6. The method according to claim 5, wherein adjusting the one of the first medical images according to the reference image includes performing upsampling or down sampling on the one of the first medical images.

7. The method according to claim 1, wherein the method is performed using a server, and further comprising storing, by the server, the incremental images and not the first medical images.

8. A method, comprising:
   determining, by a processor, incremental images of first medical images of a same region of a first object relative to a reference image, wherein each of the incremental images corresponds to a respective medical image of the first medical images, wherein each of the incremental images represents one or more determined differences between the reference image and the medical image corresponding to the incremental image, and wherein a storage space required to store the incremental images is less than a storage space required to store the first medical images;
   determining, by the processor, a first change trend of the medical images according to the incremental images, wherein the first change trend indicates a trend regarding one or more changes in the first object;
   comparing, by the processor, the first change tend with a second change trend of second medical images of a region of a second object that corresponds to the first region to obtain a similarity degree between the first change trend and the second change trend;
   sending first information to a terminal of the first object when the first change trend exceeds a preset threshold, wherein the first information indicates the similarity degree and the first change trend for the first object to make an appointment with a medical institution according to the first information;
   receiving, from a server of the medical institution, a request message for the first change trend and the incremental images; and sending, to the server and in response to the request message, the first change trend and the incremental images.

9. An apparatus comprising:
a processor configured to:
   determine incremental images of first medical images of a same region of a first object relative to a reference image, wherein each of the incremental images corresponds to a respective medical image of the first medical images, wherein each of the incremental represents one or more determined differences between the reference image and the medical image corresponding to the incremental image, and wherein a storage space required to store the incremental images is less than a storage space required to store the first medical images; and
   determine a first change trend of the medical images according to the incremental images, wherein the first change trend indicates a trend regarding one or more changes in the first object;
a transmitter coupled to the processor and configured to:
   send first information to a terminal of the first object when the first change trend exceeds a preset threshold, wherein the first information indicates the first change trend; and
   send appointment information of a medical institution to the terminal, wherein the appointment information indicates an available medical resource of the medical institution; and
a receiver coupled to the processor and configured to receive appointment confirmation information from the terminal,
wherein the transmitter is further configured to send, according to the appointment confirmation information, the first change trend and the incremental images to a server of the medical institution.

10. The apparatus of claim 9, wherein before sending the appointment information, the transmitter is further configured to:
   establish communication with the server of the medical institution; and
   acquire the appointment information, wherein the appointment information identifies a department, a time, and a doctor.

11. The apparatus of claim 9, wherein the processor is further configured to compare the first change trend with a second change trend of second medical images of a same region of a second object to obtain a similarity degree between the first change trend and the second change trend, and wherein the first information further indicates the similarity degree.

12. The apparatus of claim 9, further comprising a medical imaging device that includes the processor and the transmitter, and wherein the medical imaging device is configured to photograph the first object to generate the first medical images.

13. An apparatus, comprising:
a processor configured to:
   determine incremental images of first medical images of a same region of a first object relative to a reference image, wherein each of the incremental images corresponds to a respective medical image of the first medical images, wherein each of the incremental images represents one or more determined differences between the reference image and the medical image corresponding to the incremental image, and wherein a storage space required to store the incremental images is less than a storage space required to store the first medical images;
   determine a first change trend of the first medical images according to the incremental images, wherein the first change trend indicates a trend regarding one or more changes in the first object; and
   compare the first change trend with a second change trend of second medical images of a same region of a second object to obtain a similarity degree between the first change trend and the second change trend;
a transmitter coupled to the processor and configured to send first information to a terminal of the first object when the first change trend exceeds a preset threshold, wherein the first information indicates the similarity degree and the first change trend for the first object to make an appointment with a medical institution according to the first information; and
a receiver coupled to the processor and configured to receive, from a server of the medical institution, a request message for the first change trend and the incremental images,
wherein the transmitter is further configured to send, to the server and in response to the request message, the first change trend and the incremental images.

* * * * *

UNITED STATES PATENT AND TRADEMARK OFFICE
CERTIFICATE OF CORRECTION

PATENT NO. : 10,013,528 B2
APPLICATION NO. : 15/245572
DATED : July 3, 2018
INVENTOR(S) : Yingtao Li, Shanfu Li and Kangmin Huang Page 1 of 1

It is certified that error appears in the above-identified patent and that said Letters Patent is hereby corrected as shown below:

On the Title Page

Item (30), Line 1: "201410065001" should be "201410065001.4"

In the Claims

Column 39, Line 11: Claim 9 insert --images-- before "represents"

Signed and Sealed this
Twenty-first Day of August, 2018

Andrei Iancu
*Director of the United States Patent and Trademark Office*